(12) United States Patent
Raston et al.

(10) Patent No.: US 8,252,954 B2
(45) Date of Patent: Aug. 28, 2012

(54) PROCESSES FOR THE PREPARATION OF CALIXARENE DERIVATIVES

(75) Inventors: Colin L. Raston, South Yunderup (AU); Mohamed Makha, Beechboro (AU); Thomas Edward Clark, Northbridge (AU); Jerry L. Atwood, Columbia, MO (US)

(73) Assignees: The Curators of The University of Missouri, Columbia, MO (US); The University of Western Australia, Crawley (AU)

( * ) Notice: Subject to any disclaimer, the term of this patent is extended or adjusted under 35 U.S.C. 154(b) by 272 days.

(21) Appl. No.: 12/663,515

(22) PCT Filed: Jun. 6, 2008

(86) PCT No.: PCT/AU2008/000817
§ 371 (c)(1),
(2), (4) Date: Feb. 23, 2010

(87) PCT Pub. No.: WO2008/148168
PCT Pub. Date: Dec. 11, 2008

(65) Prior Publication Data
US 2010/0185022 A1 Jul. 22, 2010

(30) Foreign Application Priority Data
Jun. 7, 2007 (AU) .................................. 2007903085

(51) Int. Cl.
*C07F 9/38* (2006.01)
(52) U.S. Cl. ................................. 562/20; 562/8; 562/23
(58) Field of Classification Search .................. None
See application file for complete search history.

(56) References Cited

U.S. PATENT DOCUMENTS
2004/0087666 A1   5/2004   Atwood et al.

FOREIGN PATENT DOCUMENTS
WO   2006056182 A1   6/2006

OTHER PUBLICATIONS

Database CAPLUS on STN, Acc. No. 2005:374591, Ursaels et al., Acta Universitatis Cibiniensis, Seria F: Chemia (2004), 7(1), p. 71-75 (abstract).*
Database CAPLUS on STN, Acc. No. 2004:319090, Ursales et al., Journal of Optoelectronics and Advanced Materials (2004), 6(1), p. 307-313 (abstract).*
Database CAPLUS on STN, Acc. No. 1995:483719, Roundhill et al., Journal of Inclusion Phenomena and Molecular Recognition in Chemistry (1994), 19(1-4), p. 101-109 (abstract).*
Bohmer, V., "Calixarenes, Macrocycles with (Almost) Unlimited Possibilities", Angew, Chem. Int. Ed. Engl. (1995) 34, 713-745.
Lazar, A. N. 35 al., "Assembly modes in the solid state structure of the complexes of melamine mono-cations with para-calix[4]arene sulfonic acid and calix[4]arene dihydroxyphosphonic acid", New Journal of Chemistry (2006), 30, 59-64.
Witt, D. et al., "Calilx[4]arene Phosphonates—Recognition of Amino Alcohols in Water", Heteroatom Chemistry (2004), 15(2), 155-161.
International Search Report, PCT/AU2008/000817, dated Jul. 23, 2008.
March, J., "Advanced Organic Chemistry: Reactions, Mechanism and Structure," 4th Edition, John Wiley & Sons, New York, 1992, pp. 352-357.

* cited by examiner

*Primary Examiner* — Brian J Davis
(74) *Attorney, Agent, or Firm* — Nixon Peabody LLP

(57) ABSTRACT

A method for the preparation of calix[n]arene derivatives, in particular phosphonated calix[n]arenes. The present invention also relates to nano-structures of phosphonated calix[n] arenes.

17 Claims, 12 Drawing Sheets

PROCESSES FOR THE PREPARATION OF CALIXARENE DERIVATIVES

CROSS REFERENCE TO RELATED APPLICATIONS OR PRIORITY CLAIM

This application is a national phase of International Application No. PCT/AU2008/000817, entitled "PROCESSES FOR THE PREPARATION OF CALIXARENE DERIVATIVES", which was filed on Jun. 6, 2008, and which claims priority of Australian Patent Application No. 2007903085, filed Jun. 7, 2007.

DESCRIPTION

1. Field of the Invention

The present invention relates to a process for the preparation of calixarene derivatives, in particular phosphonated calixarenes. The present invention also relates to nano-structures of phosphonated calixarenes.

2. Background of the Invention

Cavitand type molecules contain a hydrophobic pocket, and whilst they can assemble into large nanometer-scale self-assembled architectures by means of non-covalent interactions, their ability to assemble into nano-rafts is yet to be realized. This is despite a plethora of spectacular architectures having been established for cavitands including nano-capsules which are often based around the Platonic or Archimedean solids. They can also describe complex entities found in nature such as certain types of protozoa, pollen grains and crystals.

Cavitand type molecules include C-alkylresorcin[4]arenes and C-alkylpyrogallol[4]arenes which can form hexameric capsules with an internal cavity of 1250-1375 $Å^3$. The design characteristics of such cavitands is noteworthy in limiting intramolecular hydrogen bonding, leaving some hydroxyl groups to participate in intermolecular H-bonding, resulting in interplay of the cavitands, which can favour the formation of spheroidal-like molecular capsules. Calixarenes are another class of cavitands, which can be readily sulfonated, but generally it is the sulfonate group rather than the protonated sulfonic acid group which features in building complex arrays including spheroidal like structures comprised of twelve molecules at the vertices of icosahedra or cuboctahedra. These water soluble calixarenes are also of interest in relation to their ability to act as catalysts, surfactants, host molecules, and more.

Calixarenes are cyclic phenolic oligomers wherein two adjacent phenol rings are linked together by an ortho-ortho methylene bridge. Calixarenes generally have 4, 6, or 8 phenolic rings linked together, but calixarenes having an odd number of phenolic rings also exist. Calixarenes having less than four phenolic rings are not available.

Lipid rafts are sphingolipid and cholesterol enriched domains with high order in cell membranes, and despite their fluid like behaviour, they are more ordered and tightly packed than the surrounding bilayer. There are many proposed functions of lipid rafts ranging from viral infection, pathogenesis of prion disease through to platforms for attaching proteins. Controlling the formation of synthetic nanometer-scale rafts is a major challenge, and is of interest as a route to platforms for binding biologically relevant molecules as well as potential reaction surfaces for chemical and biological transformations, amongst others.

SUMMARY OF THE INVENTION

The present invention provides processes for the preparation of phosphonated calix[n]arene derivatives which are capable of forming bilayers, assemblies and nano-scale rafts.

According to the present invention there is provided a process for the preparation of phosphonated calix[n]arenes of formula (I):

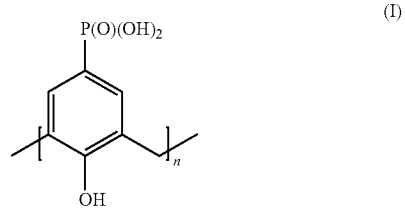

wherein n≧4, comprising the steps of:
a) reacting calix[n]arene with a source of leaving groups (Z) to produce compound (II),

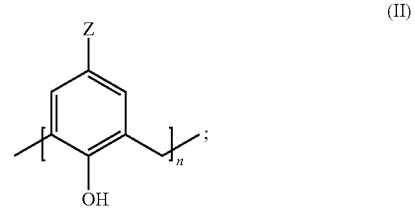

b) protecting p-hydroxyl groups of compound (II) to produce compound (III),

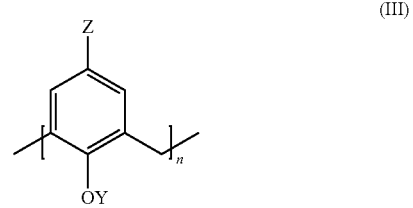

wherein Y is a protecting group;
c) reacting compound (III) with a phosphonating agent to produce compound (IV)

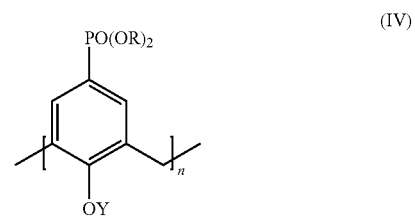

wherein R is an optionally substituted $C_1$-$C_8$ alkyl or an optionally substituted 5- or 6-membered aryl;
d) removing the protecting groups Y from compound (IV) to produce compound (V)

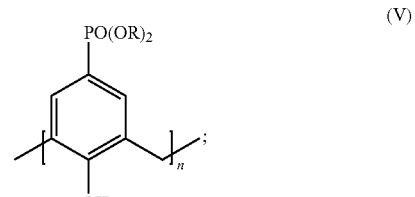

and e) de-esterifying compound (V).

Intermediates of formulas (III) and (IV) used in the preparation of compounds of formula (I) are novel and therefore also fall within the scope of the present invention.

There is also provided an alternate process for the preparation of phosphonated calix[n]arenes of formula (I):

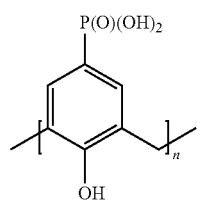
(I)

wherein n≧4 comprising the steps of:

a) protecting the hydroxyl group of a compound of formula (VI)

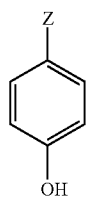
(VI)

wherein Z is a leaving group to produce compound (VII),

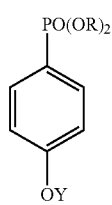
(VII)

wherein Z is a leaving group and Y is a protecting group;

b) reacting compound (VII) with a phosphonating agent to produce compound (VIII)

(VIII)

wherein Y is a protecting group and R is an optionally substituted $C_1$-$C_8$ alkyl or an optionally substituted 5- or 6-membered aryl;

c) removing the protecting group Y from compound (VIII) to produce compound (IX)

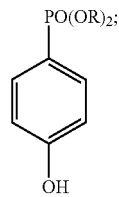
(IX)

d) de-esterifying compound (IX) to produce compound (X)

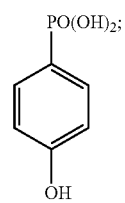
(X)

and e) reacting compound (X) with formalin and cyclising 4 or more of these compounds.

The phosphonated calix[n]arenes of formula (I) are particularly useful in forming supramolecular structures.

The present invention also provides a phosphonated calix[n]arene of formula (I) produced by either of the processes described above.

The present invention further provides phosphonated calix[n]arenes of formula (I) which are bio-compatible and/or fluorescent.

The present invention also provides a bilayer of phosphonated calix[n]arenes with each layer comprising adjacent phosphonated calix[n]arenes of formula (I):

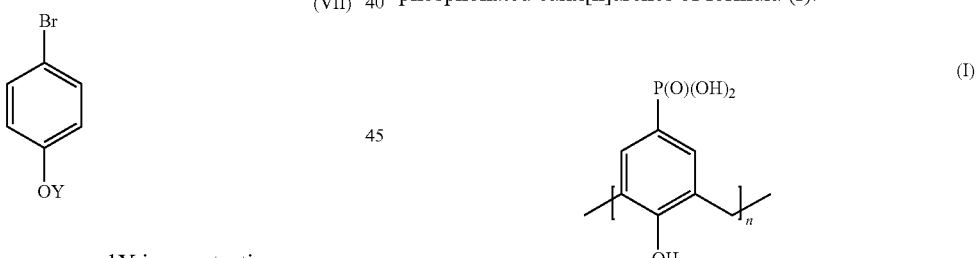
(I)

wherein n≧4,
with the two layers held together by a non-covalent bonding network.

The non-covalent bonding network includes non-covalent interactions between the phosphonate groups of the adjacent layers. The non-covalent bonding network may also include non-covalent bonds mediated by solvent molecules which are located between the bilayers.

The present invention also provides an assembly comprising a plurality of bilayers as described above wherein the plurality of bilayers are stacked together.

The present invention also provides a process for preparation of an assembly comprising evaporating a solution of the compound of formula (I) as described above. Alternatively, an assembly may also be prepared by subjecting the compound of formula (I) as described above, or a precursor to and/or reagents used to prepare the compound of formula (I) to a region of high shear. In one embodiment, a solvent which binds in the cavity of the compound of formula (I) may also be present when the compound of formula (I), or the precursor to and/or reagents used to prepare the compound of formula (I), is subjected to a region of high shear.

An assembly includes a crystallographic assembly, where the plurality of bilayers are arranged in a crystal suitable for X-ray diffraction studies. When the crystallographic assembly comprises phosphonated calix[4]arene, the calix[4]arene molecules have a crystallographically imposed symmetrical cone conformation and reside on a 4-fold symmetry axis with the tetragonal axis being located normal to the bilayers.

The assembly also includes a nanometer scale raft, which is a nanometer sized assembly which forms in the presence of a solvent which can be bound in the cavity of the compound of formula (I) described above.

The phosphonated calix[n]arene of the present invention may be used as a carrier, surfactant, coating or an enzyme mimic for catalysis.

The present invention also provides a carrier, surfactant, coating or an enzyme mimic for catalysis which is wholly or partly composed of the phosphonated calix[n]arene of formula (I) as described above.

DETAILED DESCRIPTION

Figure 1:
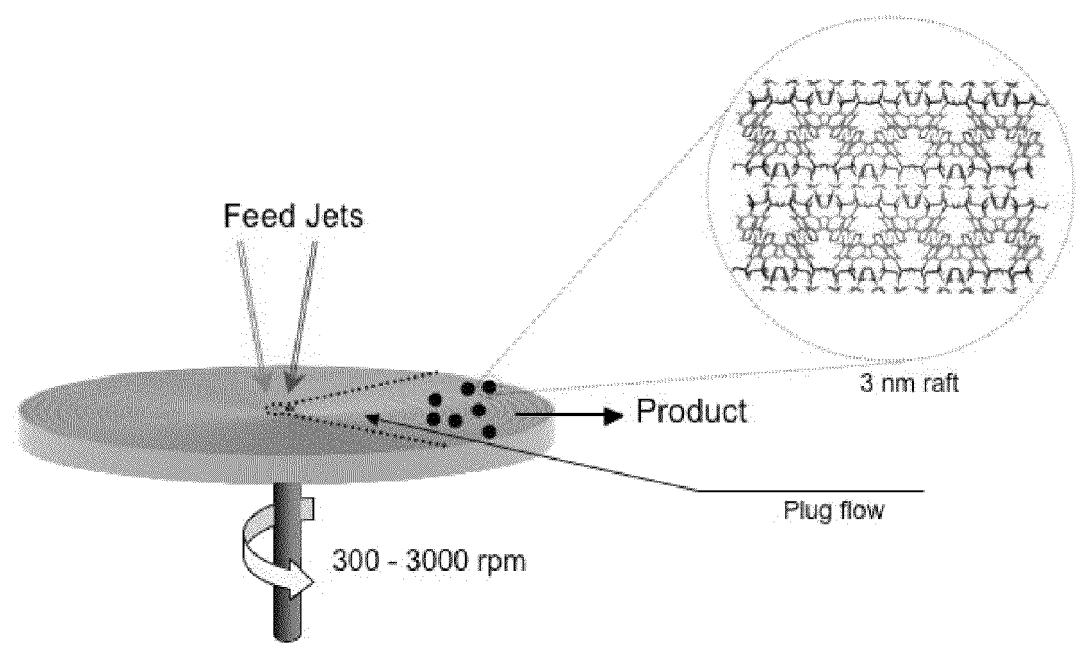
FIG. 1 is a schematic diagram showing key features of a rotating surface process (RSP), spinning disc processor (SDP) in relation to producing phosphonated calix[n]arenes in accordance with the present invention.

The present invention relates to the preparation of calixarene derivatives comprising p-substituted phosphonated calix[n]arenes of formula (I):

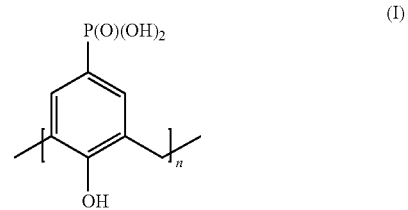

(I)

wherein n≧4, and salts thereof. Preferably n is 4 to 8. The phosphonated calix[n]arenes of formula (I) are able to form supramolecular structures which include bilayers and assemblies.

The term "phosphonated calixarene" or "phosphonated calix[n]arene" as used herein refers to p-substituted phosphonato-calix[n]arenes or p-phosphonic acid calix[n]arenes which are used interchangeably.

The lowest oligomer in the series of calix[n]arene derivatives of the present invention i.e. p-substituted phosphonated calix[4]arene has four phenol moieties. Thus p-substituted phosphonated calix[4]arene takes on the a rigid bowl shape conformation associated with four intramolecular hydrogen bonds involving the phenolic hydroxyl groups. Higher calixarenes are more flexible and may not necessarily take on a cone or bowl shape conformation.

In contrast to the p-substituted sulphonato-calixarene derivatives which are provided with only one acidic hydrogen atom for each sulphonic acid substituent, the phosphonated calix[n]arene derivatives of formula (I) hold two acidic hydrogen atoms associated with each phosphonic acid substituent. Thus, the phosphonated calix[n]arene derivatives of formula (I) demonstrate formation of bilayer arrays involving non-covalent bonding networks which include the formation of multiple hydrogen bonds associated with these groups, along with other inherently weak interactions such as π-stacking and C—H . . . π interplay.

Process for the Preparation of Calixarene Derivatives

The calixarene derivatives according to formula (I) may be prepared by a process in which a calix[n]arene is reacted with a source of leaving groups (Z) to produce the compound (II) as described above. The leaving group may be a suitable known type such as those disclosed in J. March, "Advanced Organic Chemistry: Reactions, Mechanism and Structure" 4[th] Edition, pp 352-357, John Wiley & Sons, New York, 1992 which is incorporated herein by reference. Preferably, the leaving group is halogen, more preferably bromine.

In a preferred embodiment, the source of a leaving group is a brominating agent. The brominating agent may be bromine or another suitable brominating agent which includes, but is not limited to, N-bromosuccinimide (NBS), $Br_3^-$, N-bromoacetamide, and HBr/AcOH.

The p-hydroxyl groups of compound (II) are then protected with a hydroxyl protecting group (Y) to produce compound (III) described above.

The protecting groups Y employed to protect the p-hydroxyl groups of the calix[n]arene are selected so that they will not be removed during reaction with the phosphonating agent. Hydroxyl protecting groups (Y) are independently chosen from known protecting groups used in synthetic organic chemistry. Each hydroxyl protecting group selected is preferably capable of being efficiently placed on the hydroxyl groups and is easily removed therefrom once the phosphonation reaction is completed. Suitable protecting groups are known in the art and are described in Protective Groups in Organic Synthesis, Third Edition, T. W. Greene and P. G. White, John Wiley & Sons, Inc., 1999, (the contents of which are incorporated herein by reference) as are methods for their installation and removal. Examples of hydroxyl protecting groups include ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkyl-silyl and 1,1,3,3-tetraisopropyldisiloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether protecting groups, especially t-butyldimethylsilyl; while most preferred is benzoyl. In one embodiment, the protecting groups (Y) comprise —CO—R', wherein R' is an optionally substituted $C_1$-$C_8$ alkyl. In the preferred embodiment, the protecting group (Y) is an acetyl group. The acetyl protecting groups are preferably used in the preparation of the phosphonated calix[n]arenes of formula (I) because they are easy to introduce, easy to remove after phosphorylation and inexpensive due to the use of acetic anhydride. Other protecting groups are more expensive or involve atom inefficiency. A protecting group for the hydroxyl groups is necessary in order to produce the target compounds, and also increases the solubility of the calix[n] arenes for the phosphorylation step.

In another embodiment, the protecting groups (Y) comprise silyl ethers (i.e. $R''_3Si$—, wherein R" is an alkyl group). Suitable examples of silyl ethers include, but are not limited to, TMS, TES, TIPS, TBS, TBDPS. Typically, the silyl ether protecting groups are introduced by reacting the calix[n] arene with $R''_3Si$—Cl and base. The silyl ether protecting groups are typically removed by reacting compound (IV) with fluoride sources such as tetrabutylammonium fluoride (TBAF).

In a further embodiment, the protecting groups (Y) may be selected from methoxymethyl ethers, tetrahydropyranyl ethers, allyl ethers, benzyl ethers, pivaloic acid esters and benzoic acid esters.

Compound (III), which includes the hydroxyl protecting groups (Y) is then reacted with a phosphonating agent to produce the phosphonate ester compound (IV) as described above.

Suitable phosphonating agents include, but are not limited to trialkylphosphites such as trimethylphosphite, triethylphosphite or tri-isopropylphosphite; or triarylphosphites such as triphenylphosphite. Preferably, the phosphonating agent is a trialkylphosphite, in particular triethylphosphite.

The last step involves removing the protecting groups (Y) and the phosphonate ester groups (R).

The protecting groups (Y) are removed from compound (IV) to produce compound (V) as described above. The protecting groups maybe suitably removed as known in the art and described in Protective Groups in Organic Synthesis, Third Edition, T. W. Greene and P. G. White, John Wiley & Sons, Inc., 1999, (the contents of which are incorporated herein by reference). Preferably, the protecting groups (Y) are removed by stirring compound (IV) in a mixture of KOH, methanol, tetrahydrofuran and water.

Compound (V) is finally de-esterified to produce the compound of formula (I). The phosphonate ester groups (R) may be cleaved by suitably using bromotrimethylsilane (BTMS) or iodotrimethylsilane, (ITMS). In an alternative embodiment, where the phosphonating agent is triphenylphosphite, the corresponding phosphonate ester is cleaved in a reaction using $H_2$/$PtO_2$. Preferably, compound (V) is de-esterified with bromotrimethylsilane in dry acetonitrile at reflux.

A preferred embodiment of the process for preparation of the calix[n]arenes of formula (I) is described in Scheme 1.

Scheme 1. Syntheis of p-phosphonic acid calix[n]arene.

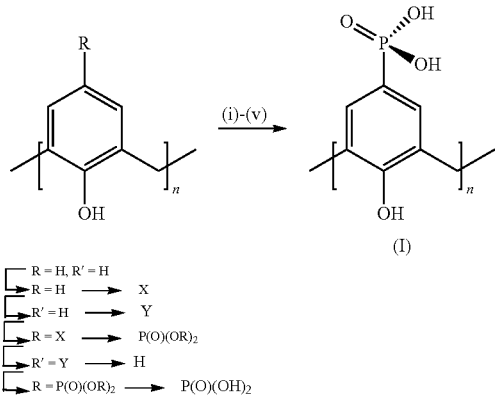

(i) R = H, R' = H
    R = H ⟶ X
(ii) R' = H ⟶ Y
(iii) R = X ⟶ P(O)(OR)$_2$
(iv) R' = Y ⟶ H
(v) R = P(O)(OR)$_2$ ⟶ P(O)(OH)$_2$ (i) Br$_2$/DMF;
(ii) (AcO)$_2$O/CH$_3$CO$_2$Na;
(iii) P(OEt)$_3$/NiCl$_2$/PhCN;
(iv) KOH/MeOH/THF/H$_2$O; and
(v) BTMS/MeCN.
DMF = dimethylformamide;
Ac = acetyl;
Et = ethyl;
Ph = phenyl;
Me = methyl;
THF = tetrahydrofuran; and
BTMS = bromotrimethylsilane.

When performed as a conventional batch-wise process, typically each step in the above synthesis yields >80% to near quantitative yield.

There is also provided an alternate process for the preparation of phosphonated calixarenes of formula (I) as described above. In a first step, the hydroxyl group of compound (VI) as described above is protected with a protecting group (Y) to produce compound (VII) as described above. Suitable hydroxyl protecting groups are as defined above, and are known in the art. The suitable hydroxyl protecting groups are described in Protective Groups in Organic Synthesis, Third Edition, T. W. Greene and P. G. White, John Wiley & Sons, Inc., 1999, (the contents of which are incorporated herein by reference) as are methods for their installation and removal.

Compound (VII) is then reacted with a phosphonating agent to produce the phosphonate ester compound (VIII) as described above. Suitable phosphonating agents are as defined above.

The protecting group (Y) is then removed from compound (VIII) to produce compound (IX) as defined above. The protecting group maybe suitably removed as known in the art and as described in Protective Groups in Organic Synthesis, Third Edition, T. W. Greene and P. G. White, John Wiley & Sons, Inc., 1999, (the contents of which are incorporated herein by reference).

Compound (IX) is de-esterified to produce the compound of formula (X) as described above. The phosphonate ester groups (R) may be cleaved by suitably using bromotrimethylsilane (BTMS) or iodotrimethylsilane, (ITMS). In an alternative embodiment, the phosphonating agent is triphenylphosphite, wherein the corresponding phosphonate ester is cleaved in a reaction using $H_2/PtO_2$. Preferably, compound (X) is de-esterified with bromotrimethylsilane in dry acetonitrile at reflux.

Finally compound (X) is reacted with formalin and is cyclised with 4 or more of these compounds. Preferably, a mixture of compound (X) formalin and acid is heated to produce the compound of formula (I). Calix[n]arenes of different sizes are isolated from the crude mixture by successive precipitations using ethyl acetate, water, dimethyl sulfoxide or a mixture with methanol or ethanol with the above mentioned solvents. The calix[n]arenes may also be isolated by chromatographic separation.

Bilayers of Phosphonated Calix[N]Arenes

The phosphonated calix[n]arenes of formula (I) are able to self-assemble into bilayers. Each layer comprises adjacent phosphonated calix[n]arenes of formula (I), and the layers are held together by a non-covalent bonding network. The non-covalent bonding network may include hydrogen bonding, solvent-mediated hydrogen bonding, non-polar interactions, π-stacking and C—H . . . π interplay.

The phosphonated-calix[n]arenes self assemble into bilayers. In one arrangement the bilayers are organised with an alternating up and down arrangement of these truncated cone shaped bucket molecules in continuous flat sheets to maximise the hydrophobic and hydrophilic interactions. This arrangement is generally applicable when n is 4 or 5 but also features in the mode of packing for higher ring sizes such as when n is 6 to 8.

We will now discuss these arrangements with reference to a specific embodiment of the invention in which n is 4 in the compound of formula (I).

Figure 2:
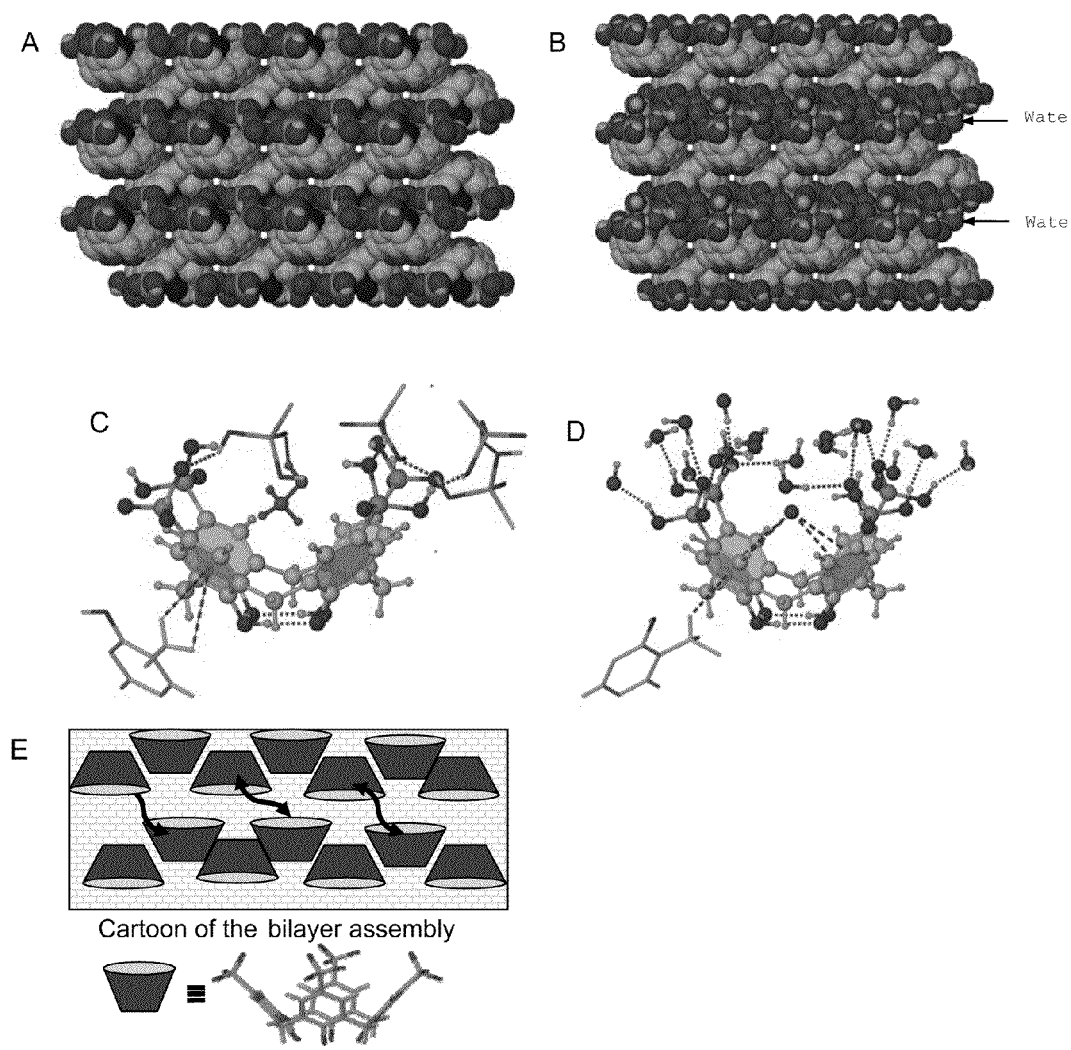
FIG. 2 (A) shows a space filling representation of the compact bilayer organization of p-phosphonated calix[4]arene (in structure 1a); (B) shows a space filling representation of the expanded bilayer organization of p-phosphonated calix[4]arene (in structure 1b); (C) shows a ball and stick representation of the building block for the bilayer in structure 1a; and (D) shows a ball and stick representation of the building block for the bilayer in structure 1b. Both (C) and (D) show the hydrogen bonding involved in the construction of the bilayers (ball and stick for one calixarene unit shown in ball and stick representation with the neighbouring calixarene fragments shown in stick representation; water and methanol molecules are depicted in blue and dashed lines represent hydrogen bonds) (E) is a schematic diagram of a plurality of stacked bilayer arrays of phosphonated calixarenes in accordance with the present invention.

FIG. 2 shows the organisation of phosphonated calix[4]arenes into bilayers under two different conditions. FIG. 2A is a space filling representation of the organisation of phosphonated calix[4]arene into a bilayer in the presence of methanol/6N $HNO_3/Cu(NO_3)_2$ and FIG. 2C shows the non-covalent bonding network that holds together the layers of the bilayer under those conditions. FIG. 2B is a space filling representation of the organisation of phosphonated calix[4]arene into a bilayer in the presence of water/curcumin and FIG. 2D shows the non-covalent bonding network that holds together the layers of the bilayer under those conditions.

In one embodiment, the overall structure, shown in FIG. 2A, is a compact bilayer arrangement with the bilayers held together by hydrogen bonding between phosphonic acid groups from different bilayers.

The structure of 1b is very similar to that of 1a, taking on the same bilayer arrangement, albeit now with the bilayers separated by a layer of water molecules, FIGS. 2 (A and B).

The bilayer arrangements in both structures have calixarenes orientated in opposite directions, FIGS. 2 (A and B). Both bilayers involve intricate hydrogen bonding networks formed by bridging methanol or water molecules between phosphonic acid moieties within each bilayer (O—H . . . $OCH_3$ distances, 1.78-2.05 Å for 1a and O—H . . . $OH_2$ distances, 1.67-1.95 Å for 1b), FIGS. 2 (C and D). In addition methanol and water embedded in the cavity of both structures interacts with the inner walls of the calixarene via CH or OH . . . interactions (short contacts for HOC . . . centroid and $H_2O$ . . . centroid are 4.01 Å and 4.08 Å, 1a and 1b respectively). The closest distance between phosphorus atoms of neighbouring bilayers is 4.62 Å in 1a whereas it is 6.20 Å in 1b where there is no hydrogen bonding between phosphonic acid groups across different bilayers. In 1a the phosphonic acids are engaged in a complex hydrogen bonding array forming a compact bilayer with short contact —POH . . . O═P(OH)$_2$ of 1.61-1.75 Å whereas in 1b water molecules in the hydrophilic layer are interposed between bilayers with $OH_2$ . . . O═P(OH)$_2$ 1.88-1.95 and $H_2O$ . . . HOPO(OH) distances ranging from 1.88-2.23 Å, FIGS. 2 (C and D). A subtle difference in the packing of calixarenes within the bilayers is that in 1a two methylene protons from a single carbon atom of one calixarene reside close to the face of an aromatic ring of another calixarene ($CH_2$ . . . π interplay) whereas in 1b only one of the H-atoms from the same methylene group is associated with such interaction.

Assemblies Comprising Calix[N]Arenes

As described above, calix[n]arene compounds of formula (I), self-assemble into bilayers, and these bilayers can stack together to form an assembly.

The assembly may be present in a crystal of micron-size which is suitable for X-ray diffraction, a micron-sized particle or a nanometer-sized particle (a nano raft).

The assemblies may be formed by evaporating a solution comprising the phosphonated calix[n]arene of formula (I) or by subjecting the phosphonated calix[n]arene of formula (I) to a region of high shear. It is also possible to provide a precursor to and/or reagents used to prepare the phosphonated calix[n]arene of formula (I) to a region of high shear.

The region of high shear may be generated using any suitable known apparatus such as a rotating surface process (RSP), spinning disc processor (SDP), rotating surface reactor and thin film technologies such as spin coating. Rotating surface reactors may be in the form of spinning disc reactors, spinning cone reactors, rotating tube reactors, and other shaped reactors as discussed in WO 2000/048728, WO 200/048730, WO 2000/048731, WO 2000/048732, and WO 2001/060511. Non-limiting examples of methods of operation of said rotating surface reactors suitable for use in the processes of the present invention are disclosed in WO 2003/008083 the full disclosure of which is also hereby incorporated into the present application by reference. Non-limiting examples of rotating surface reactors suitable for use in the processes of the present invention are disclosed in the above patent applications, the full disclosures of which are hereby incorporated into the present application by reference.

A specific example of the rotating surface reactor is shown in FIG. 1. The key components of a rotating surface reactor includes: (i) a rotating surface with controllable speed, and (ii) feed jets located at a predetermined radial distance from the centre of the surface. A very thin fluid film (1 to 200 μm) is generated on a rapidly rotating surface (10 to 3000 rpm), within which fabrication of crystals, micro-particles or nano-particles of p-phosphonated calixarenes of formula (I) is achieved (FIG. 1). The reagents, or the solutions from which compound (I) is to be crystallized, may also be delivered to the rotating surface where they are accelerated by viscous drag until an inverse hydrostatic jump occurs and a very thin fluid film (1-200 micron) spreads across the rotating surface.

The rotating surface reactor is operated so that the rotating surface spins at a speed sufficient to cause the compound of formula (I) or reactants capable of forming a compound of formula (I) as well as said one or more reagents to spread over the rotating surface as a continuously flowing thin film.

The thinness of the film contributes to many influential chemical processing characteristics, one being a very high surface area to volume ratio, resulting in more favourable interactions between the film and its surroundings. The thin film permits uniform heat transfer throughout the entire reaction mixture whereas the ability for such efficient heat conduction and convection is absent in a batch reactor. In addition, strong shearing forces create turbulence and break the surface tension of the film, making waves and ripples. These waves and ripples add to the vigour of mixing and combining the precursors and/or reagents for production of the phosphonated calix[n]arene of formula (I), or the solutions from which the phosphonated calix[n]arene of formula (I) is to be crystallized, enabling very high heat and mass transfer rates in the film. This in turn ensures extremely short reaction residence times enabling impulse heating and immediate subsequent cooling, and plug flow identifying even mixing and transfer through the entire film.

The speed of rotation of the rotating surface and the feed rate at which the compound of formula (I) or precursors to and/or reagents used to prepare a compound of formula (I), or the solutions from which compound (I) is to be crystallized, are introduced onto the rotating surface can be modified by the operator to meet the requirements of the reaction process. For example, depending upon the time necessary for the reaction to reach completion, the viscosity of the reaction mixture, or the rotational velocity can be adjusted to shorten or lengthen the residence time of the precursors to and/or the reagents used to prepare the phosphonated calix[n]arenes of formula (I), or the solutions from which compound (I) is to be crystallized, on the rotating surface or the thickness of the thin fluid film formed on the rotating surface. In one embodiment, the rotating surface has a velocity in the range of 10-3000 rpm.

Advantageously, a feature of rotating surface process technology is that it is convenient for continuous flow production which facilitates scale up, avoiding the use of batch technology where there is often the need to separate mixtures.

Rotating surface processing (FIG. 1) can employ a rapidly rotating (5-3000 rpm) disc manufactured from 316 stainless steel or other material with PTFE composite seals onto which surface reagents can be delivered through a number of different feed jets. Highly effective turbulent micro-mixing occurs as the reagents propagate across the rotating disc surface under the influence of centrifugal forces.

The reaction temperature is controlled by a recirculation coolant system that permits both heating and cooling of the rotating disc surface. Both smooth and grooved stainless steel rotating surfaces can be utilized for operation though grooved rotating surfaces have demonstrably superior wetting characteristics.

Effective throughputs range from 0.3 to 3.5 ml/s for low viscosity solvents delivered using continuous gear pumps and residence times within the reactor are commonly less than 1 second (in respect of 100 mm diameter rotating disc). Lower feeds and/or rotational speeds are prone to form rivulets rather than the requisite fluid film, whilst larger feed rates will require too large a spin up zone.

The bilayers present in the assembly may be separated by a layer of solvent molecules as seen in the structure 1b of FIG. 2 or the more compact bilayer shown in structure 1a of FIG. 2. The bilayer arrangement that is present in the assembly will depend on which solvents are present when the phosphonated calix[n]arenes are subjected to the rotating disc surface. The layer of solvent molecules may arise by inclusion of a respective solvent molecules, at least in part, in the cavity of each calixarene derivative in the bilayer array. Examples of a plurality of stacked bilayer arrays, without and with a layer of solvent molecules interspersed between each bilayer array are illustrated in FIGS. 2A and 2B, respectively.

Whether the calix[n]arene derivatives of formula (I) are subjected to the rotating disc surface in the presence or absence of a solvent capable of being bound in the cavity of the phosphonated calix[n]arene will determine whether the assembly will form a micron sized particle or a nanometer sized particle.

Crystallographic Assembly

Crystallisation of the phosphonated calixarene derivatives of formula (I) can be achieved by evaporating a solution of the calixarene derivative. Preferably, the phosphonated calix[n]arenes of formula (I) are evaporated from an aqueous or alcoholic solution. Metal cations, such as Cu(II), Ni(II), Cs(I), and Rb(I), or organic molecules such as curcumin, β-carotene, or carboranes may also be present.

Both of the structures shown in FIGS. 2A and 2B crystallize in the same tetragonal space group P4/n. The major difference between the bilayer of FIGS. 2A and 2B is in cell dimensions being associated with the tetragonal c axis, which are 11.067(3) and 14.0678(8) Å respectively. The tetragonal axis is normal to the bilayers with the cone shaped calix[4] arenes residing on four fold symmetry axes, and thus the difference in c is associated with the incorporation of a layer of water molecules for 1b relative to 1a. The a (and b) axes for the two structures are very similar (12.130(4) and 11.938(6) Å, 1a and 1b respectively), which reflects the similarity in packing within the bilayers in the two structures. In 1a there is inclusion of a disordered methanol molecule in the cavity of the calixarenes with the methyl group directed towards the cavity. Similarly, in structure 1b the cavity of each calixarene takes up a disordered water molecule. In both structures the calixarene adopts a crystallographically imposed symmetrical cone conformation. This contrasts with a partially pinched cone conformation containing an ordered water molecule in the cavity of sulfonated calixarene, which involves O—H . . . π interactions (21). In both structures the phenolic hydroxyl groups at the lower rim of the calixarene are engaged in a circular hydrogen bonded network equally disordered in opposite directions (O—H . . . O distance, 1.82 and 1.83 Å for 1a and 1b respectively).

Phosphonated calixarenes of formula (I) may also be crystallized using any suitable known apparatus such as a rotating surface reactor as described above. Preferably, an alkaline solution containing phosphonated calix[n]arene and an HCl solution at different concentrations (1.0 M, 1.5 M, 3.0 M, 6.0

M) are combined using the rotating surface reactor. The alkaline solution of phosphonated calix[n]arene is injected from one feed jet, and a solution of HCl is injected from the other feed jet at room temperature (1 ml/s, grooved disc, 1500 rpm disc rotation) to ensure an acidic solution upon mixing. This provides rapid crystallisation of the calix[n]arene assembly, and is dependent on the concentrations of HCl used.

Nanometer Scale Rafts

Nanometer scale rafts may be formed when a plurality of bilayer arrays of the calixarene derivatives of formula (I) are stacked. As described above, in one arrangement the bilayers are organised with an alternating up and down arrangement of these truncated cone shaped bucket molecules in continuous flat sheets to maximise the hydrophobic and hydrophilic interactions. This arrangement is generally applicable when n is 4 or 5 but also features in the mode of packing for higher ring sizes such as when n is 6 to 8. The layers are coupled together by non-covalent bonding interactions between phosphonic acid groups and/or solvent mediated interactions with the adjacent bilayer array. The bilayers are stacked together and the assembly is of nanometer size (i.e. a nano-scale raft).

The nanometer sized particles of the phosphonated calixarenes of formula (I) can be obtained when the assembly is formed in the presence of a polar organic solvent capable of binding in a cavity of the phosphonated calixarene of formula (I). Suitable polar organic compounds include but are not limited to any alkyl nitrile such as acetonitrile; propionitrile or butyronitrile; aryl nitrile; cycloakyl nitrile; alkenyl nitrile; alcohols such as methanol and ethanol; halogenated solvents such as chloroform, dichloromethane, carbon tetrahalide for example carbontetrachloride or carbontetraiodide; and aromatic solvents such as toluene, benzene, xylene, mesitylene and their halogenated analogues. Preferably, the polar organic solvent is an alcohol such as methanol or an alkylnitrile such as acetonitrile.

In particular, a nanometer scale raft of phosphonated calixarenes of formula (I) may be prepared by performing the last step or steps of the preparation of the compound of formula (I) in a region of high shear.

In one embodiment of the invention, the region of high shear is a rotating surface of a rotating surface reactor. Typically, the product of the reaction in which the hydroxyl protecting groups are removed and the one or more reagents to de-esterify the phosphonate esters are injected separately to the rotating surface of the rotating surface reactor, although it will be appreciated that they can be combined prior to subjecting them to high shear.

In a preferred embodiment, one or more reagents are provided to the rotating surface reactor as a liquid or a liquid dispersion thereof.

The nanometer scale rafts are produced using the rotating surface reactor involving a 1 M sodium hydroxide solution containing phosphonated calix[n]arene and an HCl solution at different concentrations (1.0 M, 1.5 M, 3.0 M, 6.0 M). The alkaline solution of phosphonated calix[n]arene is injected from one feed jet, and a solution of HCl which contains a polar organic compound as defined above is injected from the other feed jet at room temperature (1 ml/s, grooved disc, 1500 rpm disc rotation) to ensure an acidic solution upon mixing.

In one embodiment of the invention, the phosphonated calix[n]arene is phosphonated calix[4]arene and the HCl solutions contain 10% acetonitrile. Under these conditions 3.0(3) nm or 20(2) nm particles (nano-rafts) are formed (as determined by Dynamic Light Scattering). The size of the particles is dependent on the concentration of the acid.

Figure 3:
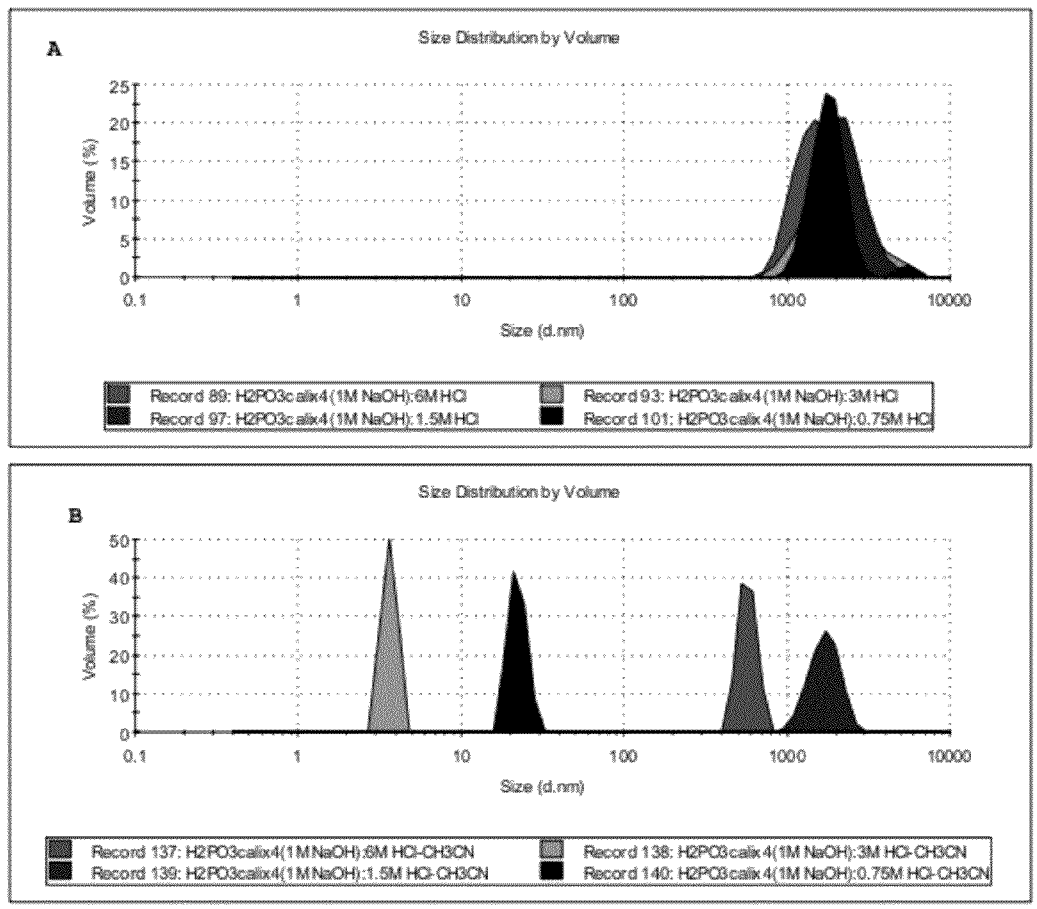
FIG. 3 shows volume size distributions of phosphonated calix[4]arene nano-particle dispersions prepared with HCl solutions at different concentrations using a spinning disk processor in accordance with the present invention.

The presence of acetonitrile circumvents the formation of micron size particles, affording stable 3.0(3) and 20(2) nm particles, 3.0 M HCl and 1.0 M HCl respectively, as shown in FIG. 3. Moreover, the particle size can also be controlled by varying the speed of the disc, amongst other parameters, for example, at 2000 rpm disc speed, 80(7) nm particles are formed for 1 M HCl, and the use of acetonitrile as a stabilizing agent/surfactant in conjunction with the rotating surface reactor is critical (Supplementary Information). Acetonitrile was selected for this purpose because of its ability to bind in the cavity of the calixarene, and could be substituted with any of the polar organic solvents described above. The acetonitrile is able to bind in the cavity at the surface of the nano-particles with the polar group directed to solution space in the same way as methanol does in 1a.

Figure 4:
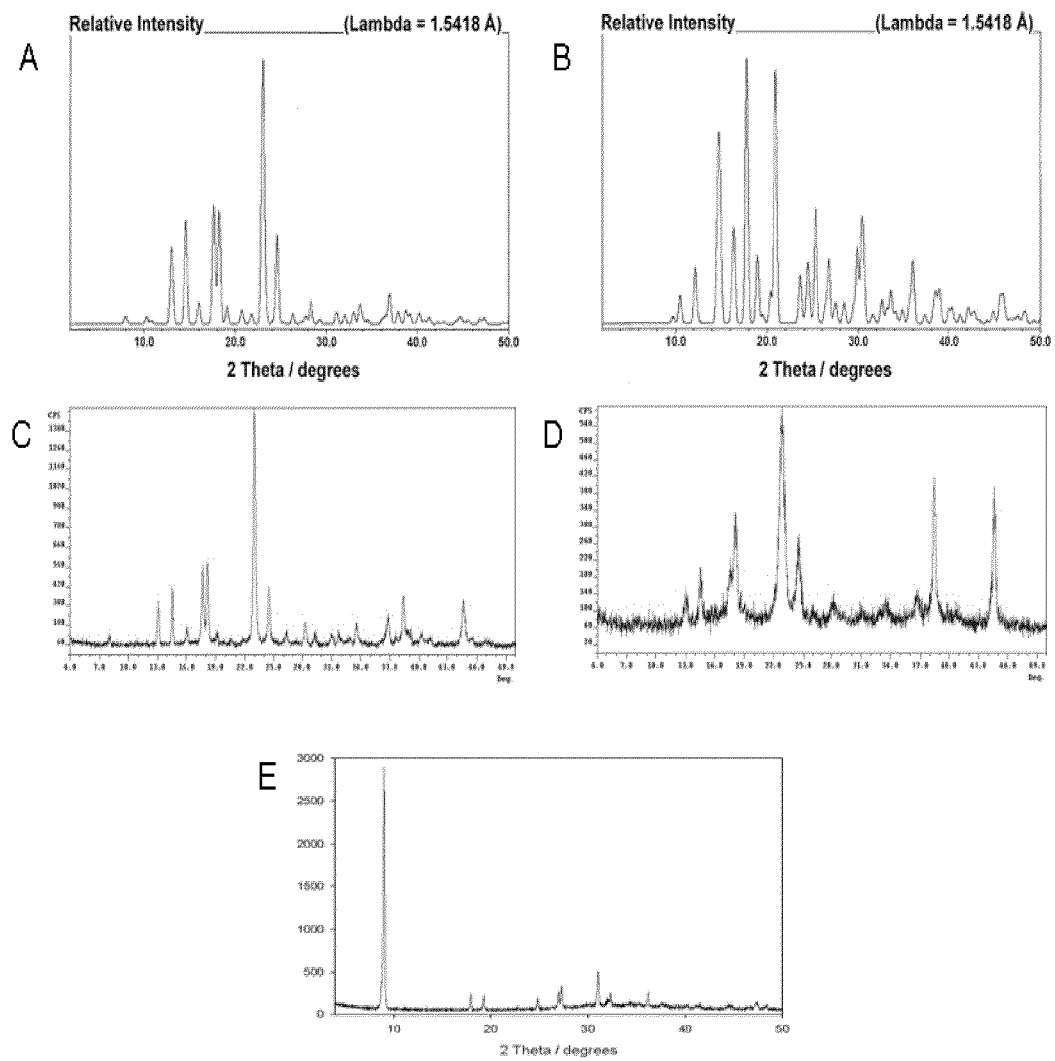
FIG. 4 shows an X-ray powder diffraction (XRPD) pattern for phosphonated calix[4]arene in accordance with the present invention.

The X-ray powder diffraction (XRPD) pattern for the as synthesized, Scheme 1, compound p-phosphonic acid calix [4]arene matches the predicted powder pattern for the aforementioned structure 1a (22), FIG. 4. Analysis of the peak widths using the Scherrer equation gave a particle size, 16-30 nm, which is comparable to that of the 20(2) nm particles formed by the rotating surface reactor. Precipitation of an aqueous solution of p-phosphonic acid calix[4]arene with excess concentrated HCl produced a solid with the same crystal packing as the as synthesized compound p-phosphonic acid calix[4]arene. Thus the packing of the calixarenes in the as synthesized product is similar to the compact bilayer as seen for structure 1a. Removal of the solvent for the above prepared 3.0(3) nm particles (without acetonitrile) gave a diffraction pattern with a dominant peak at 2 9.0° which equates to a d spacing of 1.0 nm, and matches closely the bilayer spacing in the compact bilayer, 1a, FIG. 4F.

Figure 5:
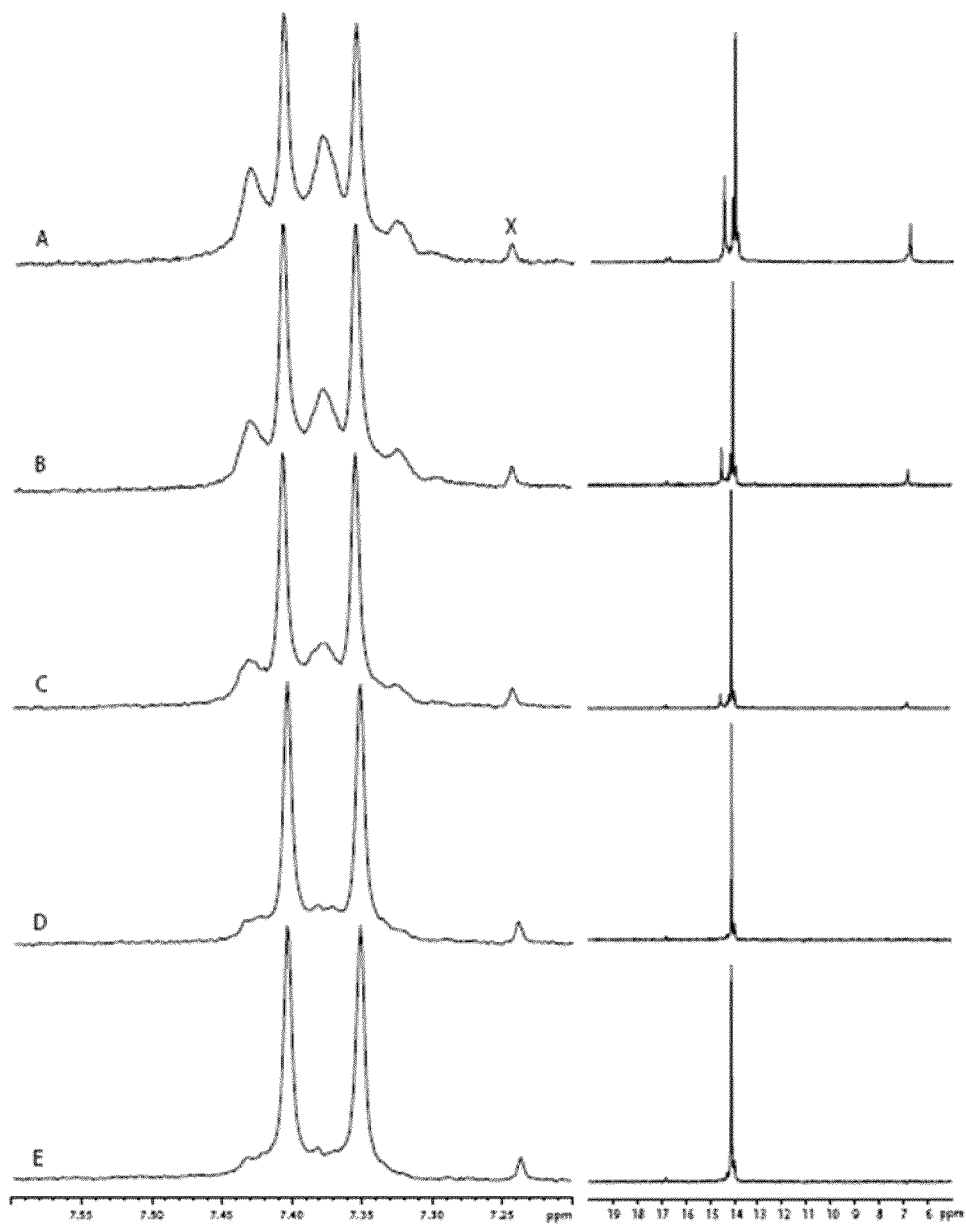
FIG. 5 shows $^1$H and $^{31}$P NMR spectra of phosphonated calix[4]arene in accordance with the present invention.

The nano-raft assemblies also show remarkable stability in DMSO at room temperature, contrary to the fact that DMSO is effectively competing for hydrogen bond formation with the calixarene. Calixarene dimers have been shown to "denature" within seconds of addition of a few % of DMSO, which disrupts the hydrogen bonded array holding the dimer together (23). Thus our present system is intriguing as the nano-rafts slowly dissociate over the course of 36 hours into solvated monomeric units, FIG. 5. A fresh deuterated DMSO solution of p-phosphonic acid calix[4]arene gives a series of doublets for the two equivalent aromatic protons split by the single phosphorus environment in the $^1$H NMR spectrum. Over time the monomer doublet becomes dominant as DMSO breaks up the nano-rafts. This is confirmed by $^{31}$P NMR showing a series of multiplets around 7 and 14 ppm which converge to a singlet at 14.7 ppm for the monomeric unit. The formation of nano-rafts does not depend on the concentration or pH of the solution but surprisingly its formation is sensitive to the presence of trace amounts of acetonitrile. One plausible explanation for this observation is that the residual acetonitrile in the as synthesized solid is orchestrating the nano-rafts assembly. Acetonitrile has been shown to form a variety of hydrogen bonds with phenol in solution (24), inclusion complexes with calixarenes (25) and as surfactant stabilizers. Dynamic solution studies were attempted to establish the size of the nano-rafts via $^{31}$P diffusion ordered spectroscopy (DOSY), however due to the slow diffusing nature of the calixarene in DMSO the technique was not suitable. p-phosphonic acid calix[4]arene has solubility limitations with the exception of protic solvents where nano-rafts are not evident.

Figure 6:
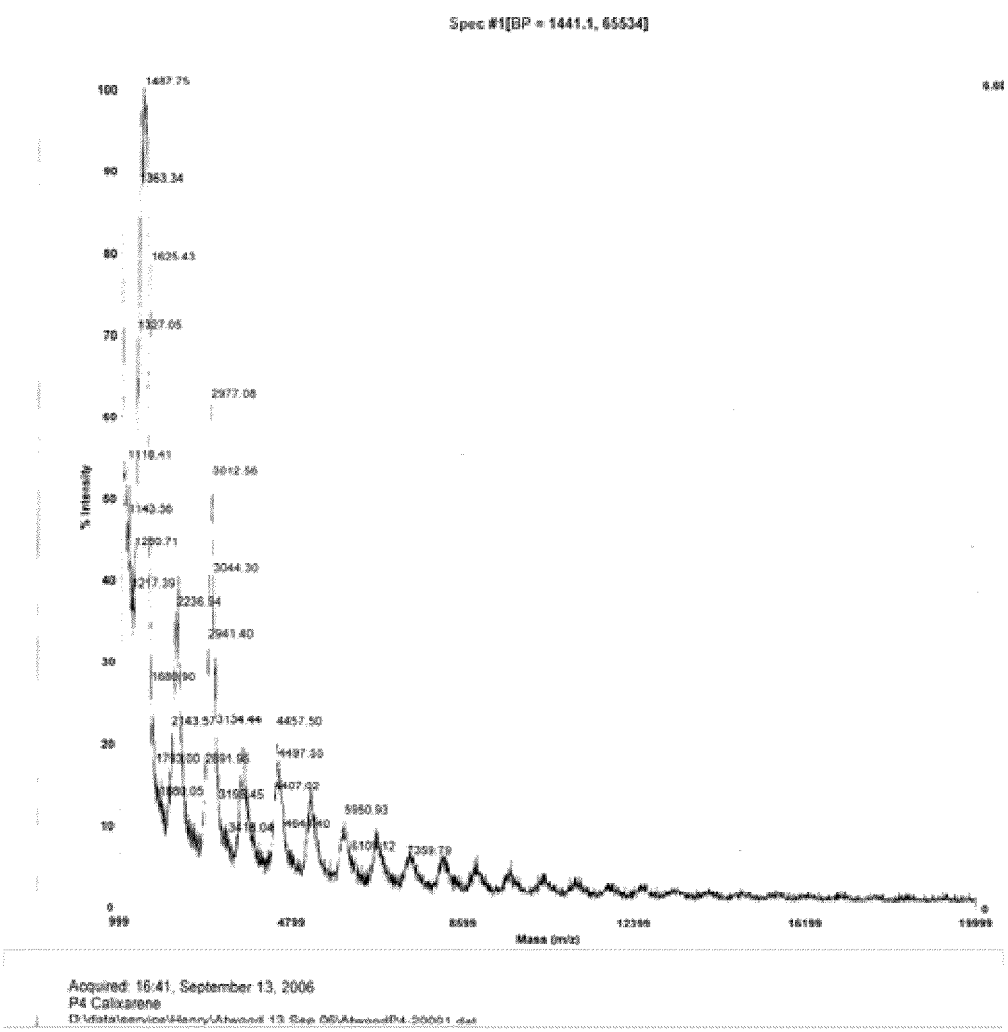
FIG. 6 shows a MALDI-TOF spectrum of phosphonated calix[4]arene in accordance with the present invention.
Figure 7:
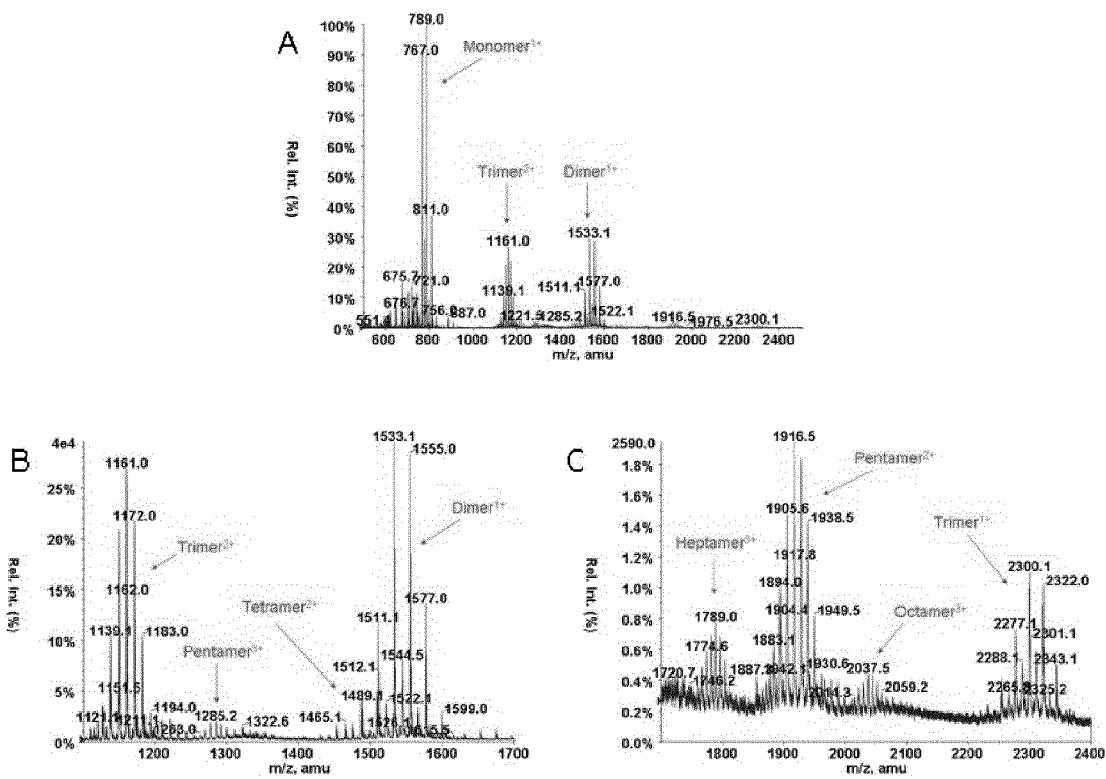
FIG. 7 shows ESI mass spectra of phosphonated calix[4]arene indicating multiply charged nano-scale raft assemblies thereof in the gas phase.

MALDI-TOF mass spectrometry on p-phosphonic acid calix[4]arene gave further evidence for the compact bilayer packing in the solid state, showing fragmentation of the bilayer devoid of solvent, FIG. 6. The nano-rafts were observed only when using an acidic matrix such as dihydroxybenzoic acid (DHB) and successive peaks out to the 20-mer were obtained. This is consistent with fragments of the continuous structure in complex 1a being generated in the gas phase by the laser. These nano-rafts can be viewed as fragments of the bilayers with aggregates of 4 and 6 molecules of p-phosphonic acid calix[4]arene showing particular stability. Attempts at detecting larger fragments by increasing the extraction delay time and decreasing the laser power, were to no avail. These results are confirmed by ESI mass spectrometry in water or methanol showing aggregates of up to 8 molecules, also with no sign of associated solvent molecules, FIG. 7. The nature of the structure of 1a rules out the likelihood of formation of spheroidal arrays of calixarenes such as the Platonic and Archimedean solids, found in the p-sulfonato-calix[4]arene arrays of 12 calixarenes with all the cavities pointing away from the core of the arrays (6-8). In addition there are no magic number signals in the mass spectrum corresponding to such structures. There is no evidence for the formation of nano-arrays of the water containing complex 1b in the gas phase.

Applications

The phosphonated calix[n]arenes of formula (I) are water soluble, bio-compatable, host molecules which are suitable for use in a range of applications. These compounds possess cavities or clefts capable of binding guest molecules of appropriate electronic or steric complimentarity. The phosphonated calix[n]arenes of formula (I) are the building blocks of the formation of supramolecular complexes, bilayers, assemblies and nano-scale rafts.

The phosphonated calix[n]arenes have the potential to form nano-scale capsular assemblies via hydrogen or coordination bonding. In one embodiment, a phosphonated calix[4]arene has been shown to form discrete 1:1 molecular capsules with complementary tetra-cationic calixarenes. The larger the $pK_a$ difference between the two pre-organized calix[n]arene building blocks, the larger the binding constant observed. The molecular capsules, have an internal volume capacity of 170-230 $Å^3$, and are very stable. These properties and the fact that phosphonated calix[n]arenes are host molecules with a cavity makes them suitable for use as carriers for guest molecules and as an enzyme mimic for catalysis. Phosphonated calix[n]arenes are efficient regioselective catalysts acting as phase transfer agents for a wide range of organic reactions which include but are not limited to nitration, sulfonation and halogenation of aromatic compounds. The mode of action is by stabilising the substrate within the cavity or within a micellar assembly for a regio attack of the reagent.

The phosphonated calix[n]arenes of formula (I) are amphiphilic compounds in that they contain both hydrophobic groups (the ring of linked para-substituted benzene moieties) and hydrophilic groups (the phosphonate and hydroxyl groups located at the rim of the calix[n]arenes). The phosphonated calix[n]arenes of formula (I) are therefore suitable for use as surfactants.

The phosphonated calix[n]arenes of the present invention may also be useful as coatings, wherein a bilayer of the calix[4]arene forms a coating on a surface. Phosphonated calix[n]arenes are excellent surfactants in stabilising nanoparticles of organic, metallic or organic/metallic hybrids in nature. Single-walled carbon nanotubes (SWCNTs) have been successfully solubilized using water-soluble p-phosphonated calix[n]arenes (n=4, 5, 6, 8). Selective SWCNT diameter solubilization has been demonstrated and subsequent preferential enrichment of SWCNTs with semiconducting or metallic electronic properties has been achieved. These water-soluble supramolecular systems can be incorporated into post-growth purification protocols with direct implications in areas such as nano-electronics and device fabrication.

In addition, the calix[n]arenes of the present invention are fluorescent. This permits the use of the phosphonated calix[n]arenes of formula (I) for targeted delivery via fluorescent drug carriers, as diagnostic tools for viruses, bacteria and other microorganisms or as contrast agents.

EXAMPLES

The invention will be illustrated in greater detail with reference to the following examples.

All starting materials and solvents were obtained from commercial suppliers and used without further purification except otherwise noted. Calix[4]arene was prepared as described previously in the literature (51). Acetonitrile was dried over 4 Å molecular sieves for 24 hours before use. $NiCl_2.6H_2O$ was dried at 180° C. in vacuo for 8 hours before use. All moisture-sensitive reactions were performed under a positive pressure of nitrogen. Chromatographic purification was performed using 200-400 mesh silica gel. TLC analysis was performed on silica gel plates (absorbent thickness 250 µm) containing a fluorescent indicator. Melting points were determined using sealed and evacuated capillary tubes on a Thomas-Hoover capillary melting point apparatus and are uncorrected. IR spectra were recorded as KBr pellets on a Perkin Elmer Spectrum One spectrometer or a Thermo-Nicolet Nexus 670 FT-IR E.S.P. $^1$H NMR (600, 500, 300 and 250 MHz), $^{13}$C NMR (151 and 126 MHz) and $^{31}$P NMR (202 and 101 MHZ) were recorded on Bruker spectrometers and internally referenced to the solvent signal or phosphoric acid for $^{31}$P NMR. FAB-MS was performed on a HP5896 mass spectrometer, ESI-MS was performed on a Finnigan TSQ7000 or ABI QStar mass spectrometer. X-ray powder diffraction data was collected on an X2 Advanced Diffraction System (Scintag Inc. USA) or a Siemens D500 diffractometer using Cu—$K_α$ ($λ$=0.154 nm). Elemental analysis was performed at The Campbell Microanalytical Laboratory, Otago, New Zealand or Galbraith Laboratories, TN, USA. The X-ray diffracted intensities were measured on an Oxford Diffraction Xcalibur CCD diffractometer or a Bruker SMART 1000 diffractometer using monochromatized Mo—$K_α$ ($λ$=0.71073 Å). Dynamic light scattering was performed on a Zetasizer Nano ZS series (Malvern Instruments) with a 532 nm laser wavelength and a measurement angle of 173° (backscatter detection) at 25° C.

Example 1

Preparation of 5,11,17,23-Tetra(dihydroxyphosphoryl)-25,26,27,28-tetrahydroxycalix[4]arene Preparation of 5,11,17,23-Tetrabromo-25,26,27,28-tetrahydroxycalix[4]arene (3)

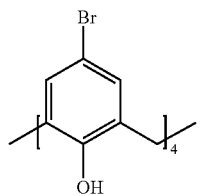

7.25 ml (0.14 mol) of Bromine in 100 ml of DMF was added drop-wise with stirring to a solution of 10.00 g (23.58 mmol) of calix[4]arene in 400 ml of DMF. The solution was stirred for 4 hours with a precipitate forming after about 0.5 hours. 400 ml of methanol was added and the mixture left to stir for 0.5 hours. The precipitate was filtered off and washed with methanol (3×50 ml) to yield 15.16 g (87%) of 3 as a white solid. $^1$H NMR (DMSO-$d_6$, 25° C., 300 MHz): δ 7.35 (s, 8H, ArH), 3.82 (br s, 8H, ArCH$_2$Ar).

Preparation of 5,11,17,23-Tetrabromo-25,26,27,28-tetraacetoxycalix[4] arene (4)

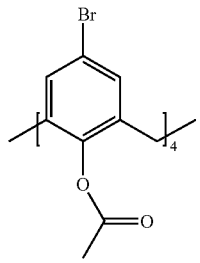

A mixture of 7.32 g (9.94 mmol) of 3 and 4.89 g (59.65 mmol) of anhydrous sodium acetate in 120 ml of acetic anhydride was refluxed for 4 hours. After cooling to RT the solution was slowly quenched with 150 ml of water. The precipitate was filtered off and washed with methanol (3×30 ml) to yield 7.72 g (86%) of 4 as a white solid. Recrystallisation from chloroform yielded X-ray quality single crystals, 4a, which were also submitted for microanalysis. m.p.>290° C. (decomp.); IR (KBr): =2919 (w), 1753 (s), 1571 (w), 1458 (m), 1368 (m), 1211 (s), 1179 (s), 873 (m) cm$^{-1}$; $^1$H NMR (CDCl$_3$, 25° C., 600 MHz): δ 7.22 (s, 8H, ArH), 3.65 (s, 8H, ArCH$_2$Ar), 1.74 ppm (s, 12H, CH$_3$); $^{13}$C NMR (CDCl$_3$, 25° C., 151 MHz): δ 167.43, 147.24, 134.82, 132.20, 118.67, 37.04, 20.22; HRMS (FAB) m/z calcd for (C$_{36}$H$_{28}$Br$_4$O$_8$+H)$^+$ 908.8555, found 908.8518; Anal. Calcd for C$_{36}$H$_{28}$Br$_4$O$_8$: C, 47.61; H, 3.11, found: C, 47.98; H, 3.36. Crystal/refinement details for 4a: C$_{39}$H$_{31}$Br$_4$Cl$_9$O$_8$, M$_r$=1266.33, F (000)=1244 e, triclinic, P$\bar{1}$(No. 2), Z=2, T=153(2) K, a=13.171(2), b=13.487(2), c=15.014(2)Å, α=95.498(2), β=93.609(2), γ=114.844(2)°, V=2393.3(6)Å$^3$, ρ$_{calcd}$=1.757 g cm$^{-3}$, sin θ/λ$_{max}$=0.5953, N (unique)=8258, (merged from 16787, R$_{int}$=0.0461, R$_{sig}$=0.0634), N$_o$ (I>2σ(I))=6811, R=0.0369, wR2=0.0978 (A, B=0.04, 0.00), GOF=1.093, |Δρ$_{max}$|=1.1(1) e Å$^{-3}$.

Preparation of 5,11,17,23-Tetra(diethoxyphosphoryl)-25,26,27,28-tetraacetoxycalix[4]arene (5)

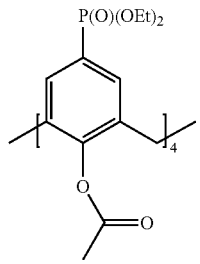

A solution of 5.51 g (6.10 mmol) of 4 and 0.79 g (6.10 mmol) of NiCl$_2$ in 10 ml of benzonitrile was treated dropwise with 10.45 ml (60.96 mmol) of P(OEt)$_3$ under nitrogen at 190° C. The solution was stirred for 0.5 hours and the volatiles removed under reduced pressure to leave an orange residue. The residue was purified by flash chromatography to yield 5.83 g (84%) of 5 as a light yellow solid. Recrystallisation from toluene or ethyl acetate yielded X-ray quality single crystals, 5a and 5b respectively, which were also submitted for microanalysis. R$_f$ 0.44 (1:4 methanol-ethyl acetate); m.p. 251-253° C.; IR (KBr): 2985 (m), 2911 (m), 1755 (s), 1650 (w), 1464 (m), 1374 (m), 1267 (m), 1020 (s), 970 (s), 796 (w), 609 (m) cm$^{-1}$; $^1$H NMR (CDCl$_3$, 25° C., 500 MHz): δ 7.52 (d, 8H, ArH, J$_{P-H}$=13.0 Hz), 4.20-4.05 (m, 16H, POCH$_2$), 3.79 (s, 8H, ArCH$_2$Ar), 1.67 (s, 12H, CH$_3$), 1.31 ppm (t, 24H, POCH$_2$CH$_3$, J=7.0 Hz); $^{13}$C NMR (CDCl$_3$, 25° C., 126 MHz): δ=167.31, 151.22 (d, $^4J_{P-C}$=4.2 Hz), 133.27 (d, $^3J_{P-C}$=16.2 Hz), 132.72 (d, $^2J_{P-C}$=10.4 Hz), 126.15 (d, $^1J_{P-C}$=192.5 Hz), 62.22 (d, $^2J_{P-C}$=6.0 Hz), 37.24, 20.07, 16.35 ppm (d, $^3J_{P-C}$=6.4 Hz); $^{31}$P NMR (CDCl$_3$, 25° C., 202 MHz): δ 17.79 ppm; HRMS (FAB) m/z calcd for (C$_{52}$H$_{68}$O$_{20}$P$_4$+H)$^+$ 1137.3333, found 1137.3363; Anal. Calcd for C$_{52}$H$_{68}$O$_{20}$P$_4$+ 1.2H$_2$O: C, 53.91; H, 6.12, found: C, 53.66; H, 5.86. Crystal/refinement details for 5a: C$_{55.50}$H$_{74}$O$_{21}$P$_4$, M$_r$=1201.03, F (000)=2540 e, triclinic, P$\bar{1}$(No. 2), Z=4, T=153(2) K, a=13.410(2), b=17.619(2), c=27.760(4) Å, α=103.086(2), β=91.709(2), γ=108.046(2)°, V=6038.8(14)Å$^3$, ρ$_{calcd}$=1.321 g cm$^{-3}$, sin θ/λ$_{max}$=0.5946, N (unique)=21084 (merged from 46491, R$_{int}$=0.0386, R$_{sig}$=0.0631), N$_o$ (I>2σ(I))=14021, R=0.0689, wR2=0.1790 (A, B=0.10, 8.52), GOF=1.042, |Δρ$_{max}$|=1.4(1) eÅ$^{-3}$.

Crystal/refinement details for 5b: C$_{108}$H$_{148}$O$_{44}$P$_8$, M=2398.02, F (000)=2536 e, triclinic, P$\bar{1}$(No. 2), Z=2, T=153(2) K, a=13.547(2), b=17.641(3), c=27.463(5) Å, α=102.591(2), β=92.803(2), γ=109.046(2)°, V=6003.2(17)Å$^3$, ρ$_{calcd}$=1.327 g cm$^{-3}$, sin θ/λ$_{max}$=0.5964, N (unique)=20010 (merged from 37575, R$_{int}$=0.0361, R$_{sig}$=0.0630), N$_o$ (I>2σ (I))=13894, R=0.1028, wR2=0.2774 (A, B=0.17, 17.15), GOF=1.064, |Δρ$_{max}$|1.7(1) eÅ$^{-3}$.

Preparation of 5,11,17,23-Tetra(diethoxyphosphoryl)-25,26,27,28-tetrahydroxycalix[4]arene (6)

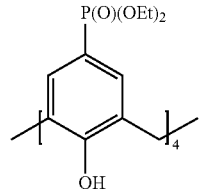

A mixture of 2.50 g (2.20 mmol) of 5 and 1.23 g (22.00 mmol) of KOH in 50 ml of methanol, 50 ml of tetrahydrofuran and 50 ml of water was stirred for 4 hours. The solvents were removed under reduced pressure and the residue treated with 50 ml of dichloromethane and 50 ml of 2$_N$ HCl. The organic layer was separated, washed with 2N HCl (1×25 ml), water (2×25 ml), dried over MgSO$_4$ and evaporated under reduced pressure to yield 2.10 g (99%) of 6 as a light yellow solid. Recrystallisation from EtOAc/hexane yielded a white solid suitable for microanalysis. m.p. 126-128° C.; IR (KBr): δ=3307 (br), 2984 (m), 2906 (m), 1599 (m), 1478 (m), 1392 (w), 1284 (m), 1022 (s), 963 (s), 790 (m) cm$^{-1}$; $^1$H NMR (CDCl$_3$, 25° C., 600 MHz): δ=10.27 (br s, 4H, OH), 7.56 (d, 8H, ArH, J$_{P-H}$=13.2 Hz), 4.26 (br s, 4H, ArCHHAr), 4.11-4.02 (m, 8H, POCHHCH$_3$), 4.02-3.94 (m, 8H, POCHHCH$_3$), 3.69 (br s, 4H, ArCHHAr), 1.27 (t, 24H, POCH$_2$CH$_3$, J=7.2 Hz); $^{13}$C NMR (CDCl$_3$, 25° C., 151 MHz): δ=152.30 (d, $^4J_{P-C}$=3.6 Hz), 133.38 (d, $^2J_{P-C}$=10.7 Hz), 127.72 (d, $^3J_{P-C}$=16.3 Hz), 122.25 (d, $^1J_{P-C}$=193.9 Hz), 62.09 (d, $^2J_{P-C}$=5.6 Hz), 31.42, 16.28 ppm (d, $^3J_{P-C}$=6.3 Hz); $^{31}$P NMR (CDCl$_3$, 25° C., 202 MHz): δ=18.73; HRMS (FAB) m/z calcd for $(C_{44}H_{60}O_{16}P_4+2H)^+$ 970.2988, found 970.2940; Anal. Calcd for $C_{44}H_{60}O_{16}P_4+0.35H_2O$: C, 54.20; H, 6.27, found: C, 53.93; H, 5.96.

Preparation of 5,11,17,23-Tetra(dihydroxyphosphoryl)-25,26,27,28-tetrahydroxycalix[4]arene (1)

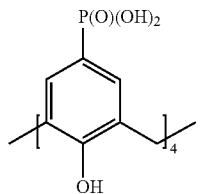

4.75 ml (36.02 mmol) of Bromotrimethylsilane was added to 2.18 g (2.25 mmol) of 6 in 50 ml of dry acetonitrile and the solution was refluxed for 16 hours. The volatiles were removed under reduced pressure and the resulting residue was triturated with 40 ml of acetonitrile and 2 ml of water. The precipitate formed was filtered off and washed with acetonitrile (3×20 ml) to yield 1.65 g (99%) of 1 as a white solid. Recrystallisation from methanol/6N $HNO_3/Cu(NO_3)_2$ or water/curcumin yielded X-ray quality single crystals, 1a and 1b respectively, which were also submitted for microanalysis. m.p. 233-235° C. (decomp.); IR (KBr): =3174 (br), 2300 (br), 1600 (m), 1473 (m), 1384 (m), 1275 (m), 1133 (s), 983 (s), 885 (m) cm$^{-1}$; $^1$H NMR (DMSO-d$_6$, 25° C., 500 MHz): δ=7.39 (d, 8H, ArH, $J_{P-H}$=13.0 Hz), 5.73 (br s, COH/POH, shifts downfield with increasing [H]$^+$), 3.93 (br s, 8H, ArCH$_2$Ar); $^{13}$C NMR (DMSO-d$_6$, 25° C., 126 MHz): δ=154.03, 131.67 (d, $^2J_{P-C}$=10.1 Hz), 127.74 (d, $^3J_{P-C}$=15.1 Hz), 124.65 (d, $^1J_{P-C}$=186.1 Hz), 31.09 ppm; $^{31}$P NMR (DMSO-d$_6$, 25° C., 101 MHz): δ=14.74; MS (ESI) m/z calcd for $(C_{28}H_{28}O_{16}P_4+H)^+$ 745.04, found 745.04; Anal. Calcd for $C_{28}H_{28}O_{16}P_4+0.5H_2O+CH_3OH$: C, 44.35; H, 4.23, found: C, 44.04; H, 4.61.

Crystal/refinement details for 1a: $C_{29}H_{33}O_{17.5}P_4$; M=785.43, F (000)=814 e, Tetragonal, P4/n, Z=2, T=173(2) K, a=b=12.130(4), c=11.067(3) Å, V=1628.4(7) Å$^3$, D$_c$=1.602 gcm$^3$, sin θ/λ$_{max}$=0.5552, N (unique)=1161 (merged from 4657, R$_{int}$=0.0615, R$_{sig}$=0.0597), N$_o$ (I>2σI))= 801, R=0.0960, wR2=0.2116 (A, B=0.09, 18.00), GOF=1.002, |Δρ$_{max}$|=1.0(1) e Å$^3$.

Crystal/refinement details for 1b: $C_{28}H_{48}O_{26}P_4$, M=924.54, F (000)=968 e, Tetragonal, P4/n, Z=2, T=100(2) K, a=b=11.9381(6), c=14.0678(8) Å, V=2004.92(15) Å$^3$, D$_c$=1.531 g/cm$^3$, sin θ/λ$_{max}$=0.5946, N (unique)=1758 (merged from 15584, R$_{int}$=0.0891, R$_{sig}$=0.0721), N$_o$ (I>2 (I))=1492, R=0.1238, wR2=0.2503 (Å, B=0.10, 13.40), GOF=1.185, |Δρ$_{max}$|=0.8(1) e Å$^{-3}$.

Example 2

Preparation of Phosphonated Calix[5]Arene

Preparation of 5,11,17,23,29-Pentabromo-31,32,33,34,35-pentahydroxycalix[5]arene (7)

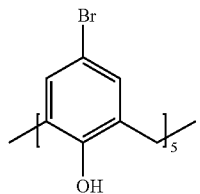

3.62 ml (70.73 mmol) of bromine in 50 ml of DMF was added drop-wise with stirring to a solution of 5.00 g (9.43 mmol) of calix[5]arene, in 200 ml of DMF. The solution was stirred for 4 h and the volatiles were removed under reduced pressure. After addition of 250 ml of methanol the precipitate was filtered off and washed with methanol (3×40 ml) to yield 8.01 g (92%) of 7 as a pale brown solid. $^1$H NMR (CDCl$_3$, 25° C., 250 MHz) δ 8.77 (s, 5H, OH), 7.31 (s, 10H, ArH), 3.75 (br s, 10H, ArCH$_2$Ar).

Preparation of 5,11,17,23,29-Pentabromo-31,32,33,34,35-pentaacetoxycalix[5]arene (8)

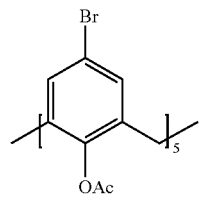

A mixture of 7.03 g (7.64 mmol) of 7 and 4.70 g (57.28 mmol) of anhydrous sodium acetate in 60 ml of acetic anhydride was refluxed for 4 h. After cooling to RT the solution was slowly quenched with 80 ml of water. The precipitate was collected by filtration and washed with methanol (3×30 ml) to yield 7.43 g (86%) of 8 as a light green solid. Recrystallisation from dichloromethane yielded X-ray quality single crystals, 8.3CH$_2$Cl$_2$.2,25H$_2$O, which were also submitted for microanalysis; mp>270° C. (decomp.); IR (KBr) 2932 (w), 1764 (s), 1574 (m), 1458 (s), 1369 (m), 1208 (s), 1173 (s), 873 (m) cm$^{-1}$; $^1$H NMR (CDCl$_3$, 25° C., 500 MHz) δ 7.76-6.68 (m, 10H, ArH), 4.02-3.02 (m, 10H, ArCH$_2$Ar), 2.74-1.10 (m, 15H, CH$_3$); $^{13}$C NMR (CDCl$_3$, 25° C., 126 MHz) δ 168.80-167.81 (m), 147.72-145.06 (m), 135.88-130.24 (m), 119.91-118.36 (m), 34.91-33.09 (m), 31.69-29.89 (m), 20.99-18.61 (m); HRMS (FAB) m/z calc. for $[C_{45}H_{35}Br_5O_{10}-H]^-$ 1132.8028, found 1132.7952. Elemental analysis. Calc. (%) for $C_{45}H_{35}Br_5O_{10}$: C, 47.61; H, 3.11. Found: C, 47.41; H, 3.02.

Crystal/refinement details for 8.3CH$_2$Cl$_2$.2.25H$_2$O. $C_{48}H_{45.5}Br_5Cl_6O_{12.25}$, M=1430.59, F (000)=5668 e, monoclinic, C2/c, Z=8, T=100(2) K, a=37.319(8), b=15.438(5), c=21.720(6)Å, β=115.70(10)°, V=11 276(5) Å$^3$, D$_c$=1.685 g cm$^{-3}$, μ$_{Mo}$=3.906 mm$^{-1}$, sin(θ/λ$_{max}$)=0.6427, N (unique)=12 406 (merged from 38 911, R$_{int}$=0.0723, R$_{sig}$=0.0839), N$_o$ (I>2σ(I))=7523, R=0.0710, wR2=0.1600 (A, B=0.06, 121.8), GOF=1.034, |Δρ$_{max}$|=0.9(1) e Å$^{-3}$. CCDC, 669055.

Preparation of 5,11,17,23,29-Penta(diethoxyphosphoryl)-31,32,33,34,35-pentaacetoxycalix[5]arene (9)

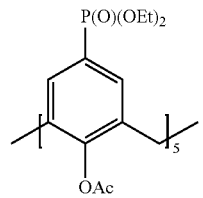

A solution of 3.87 g (3.43 mmol) of 8 and 0.56 g (4.28 mmol) of NiCl$_2$ in 20 ml of benzonitrile was treated dropwise with 7.34 ml (42.83 mmol) of P(OEt)$_3$ under nitrogen at 190° C. The solution was stirred for 0.5 hours and the volatiles removed under reduced pressure to leave an orange residue. The residue was purified by flash chromatography to yield 5.21 g of a light yellow solid. Recrystallisation from toluene-hexane yielded 4.30 g (88%) of 9 as a white solid. Further recrystallisation from toluene yielded X-ray quality single crystals, 9, which were also submitted for microanalysis. $R_f$=0.43 (1:4 methanol-ethyl acetate); mp 253-255° C.; IR (KBr) 2985 (m), 2911 (w), 1763 (s), 1653 (w), 1457 (m), 1373 (m), 1272 (m), 1020 (s), 966 (s), 796 (w), 605 (m) cm$^{-1}$; $^1$H NMR (CDCl$_3$, 25° C., 500 MHz) 8.12-7.01 (m, 10H, ArH), 4.46-3.24 (m, 30H, ArCH$_2$Ar and POCH$_2$), 2.82-0.87 (m, 45H, CH$_3$ and POCH$_2$CH$_3$); $^{13}$C NMR (CDCl$_3$, 25° C., 126 MHz) 167.93, 151.95-148.10 (m), 135.35-130.04 (m), 128.38-124.95 (m), 62.36 (d, $^2J_{P-C}$=3.6 Hz), 35.69-33.91 (m), 31.54-30.32 (m), 21.53-18.15 (m), 16.32 (d, $^3J_{P-C}$=4.2 Hz); $^{31}$P NMR (CDCl$_3$, 25° C., 101 MHz) δ 17.71; MS (ESI) m/z calc. for [C$_{65}$H$_{85}$O$_{25}$P$_5$+Na]$^+$ 1443.3966, found 1443.4003. Elemental analysis. Calc. (%) for C$_{65}$H$_{85}$O$_{25}$P$_5$·0.65H$_2$O: C, 54.48, H, 6.07. Found: C, 54.21; H, 5.78.

Crystal/refinement details for 9. C$_{65}$H$_{85}$O$_{25}$P$_5$, M=1421.18, F (000)=1500 e, triclinic, P$\bar{1}$, Z=2, T=100(2) K, a=12.9938(4), b=16.3618(5), c=18.4136(6), α=100.825(3), β=94.164(3), γ=112.261(3)°, V=3513.2(7)Å$^3$, D$_c$=1.343 g cm$^{-3}$, μ$_{Cu}$=1.873 mm$^{-1}$, sin(θ/ρ$_{max}$)=0.5970, N (unique)= 12348 (merged from 41009, R$_{int}$=0.0483, R$_{sig}$=0.0599), N$_o$ (I>2 (I))=7153, R=0.0731, wR2=0.1995 (A, B=0.145, 0), GOF=1.008, |Δρ$_{max}$|=1.63(9) eÅ$^{-3}$. CCDC, 669056.

Preparation of 5,11,17,23,29-Penta(diethoxyphosphoryl)-31,32,33,34,35-pentahydroxycalix[5]arene (10)

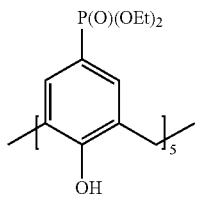

A mixture of 2.04 g (1.44 mmol) of 9 and 1.01 g (17.98 mmol) of KOH in 50 ml of methanol, 50 ml of tetrahydrofuran and 50 ml of water was stirred for 4 hours. The solvents were removed under reduced pressure and the residue treated with 50 ml of dichloromethane and 50 ml of 2 M HCl. The organic layer was separated, washed with 2 M HCl (1×25 ml), water (2×25 ml), dried over MgSO$_4$ and evaporated under reduced pressure to yield 1.70 g (98%) of 10 as a white solid. Recrystallisation from ethyl acetate-hexane yielded a white solid suitable for microanalysis; mp 128-130° C.; IR (KBr) 3365 (br), 2984 (m), 2907 (m), 1653 (m), 1473 (m), 1394 (m), 1278 (m), 1022 (s), 966 (s), 795 (m) cm$^{-1}$; $^1$H NMR (CDCl$_3$, 25° C., 500 MHz) δ 9.03 (br s, 5H, OH), 7.66 (d, 10H, ArH, J$_{P-H}$=13.0 Hz), 4.28-3.62 (m, 30H, ArCH$_2$Ar and POCH$_2$), 1.23 (t, 30H, POCH$_2$CH$_3$, J=7.0 Hz); $^{13}$C NMR (CDCl$_3$, 25° C., 126 MHz) δ 153.73, 133.32 (d, $^2J_{P-C}$=10.7 Hz), 126.77 (d, $^3J_{P-C}$=14.2 Hz), 121.20 (d, $^1J_{P-C}$=190.1 Hz), 62.07 (d, $^2J_{P-C}$= 5.2 Hz), 30.96, 16.23 (d, $^3J_{P-C}$=6.5 Hz); $^{31}$P NMR (CDCl$_3$, 25° C., 101 MHz) δ 19.21; MS (ESI) m/z calc. for [C$_{55}$H$_{75}$O$_{20}$P$_5$+Na]$^+$1233.3438, found 1233.3505. Elemental analysis. Calc. (%) for C$_{55}$H$_{75}$O$_{20}$P$_5$: C, 54.55; H, 6.24. Found: C, 54.56; H, 6.05.

Preparation of 5,11,17,23,29-Penta(dihydroxyphosphoryl)-31,32,33,34,35-pentahydroxycalix[5] arene (11)

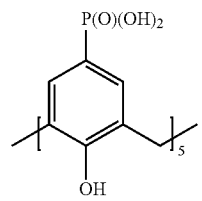

3.53 ml (26.77 mmol) of bromotrimethylsilane was added to 1.62 g (1.34 mmol) of 10 in 50 ml of dry acetonitrile and the solution was refluxed for 16 hours. The volatiles were removed under reduced pressure and the resulting residue was triturated with 40 ml of acetonitrile and 2 ml of water. The precipitate formed was filtered off and washed with acetonitrile (3×20 ml) to yield 1.23 g (99%) of 11 as a white solid. Purification using the ion exchange resin, Dowex 50W yielded a white solid suitable for microanalysis; mp>280° C. (decomp.); IR (KBr) 3393 (br), 2300 (br), 1597 (m), 1471 (s), 1385 (m), 1280 (m), 1124 (m), 950 (m), 874 (m) cm$^{-1}$; $^1$H NMR (CDCl$_3$, 25° C., 600 MHz) δ 7.42 (d, 10H, ArH, J$_{P-H}$=13.2 Hz), 5.35 (br s, COH/POH, shifts downfield with increasing [H]$^+$), 3.88 (s, 10H, ArCH$_2$Ar); $^{13}$C NMR (DMSO-d$_6$, 25° C., 151 MHz) δ 154.14, 131.74 (d, $^2J_{P-C}$= 10.3 Hz), 127.57 (d, $^3J_{P-C}$=15.4 Hz), 124.58 (d, $^1J_{P-C}$=186.1 Hz), 30.78; $^{31}$P NMR (DMSO-d$_6$, 25° C., 243 MHz) 15.03; MS (ESI) m/z calc. for [C$_{35}$H$_{35}$O$_{20}$P$_5$+H]$^+$ 931.05, found 931.13. Elemental analysis. Calc. (%) for C$_{35}$H$_{35}$O$_{20}$P$_5$·1.25H$_2$O: C, 44.11; H, 3.97. Found: C, 44.31; H, 4.18.

Example 3

Preparation of Phosphonated Calix[6]Arene

Preparation of 5,11,17,23,29,35-Hexabromo-37,38,39,40,41,42-hexahydroxycalix[6]arene (12)

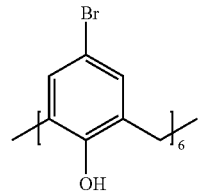

Starting from 7.25 ml (0.14 mol) of bromine in 100 ml of DMF and 10.00 g (15.72 mol) of calix[6]arene in 400 ml of DMF, 14.01 g (81%) of 12 was obtained as a white solid. $^1$H NMR (DMSO-d6, 530 25° C., 200 MHz) δ 7.11 (s, 12H, ArH), 3.78 (s, 12H, ArCH2Ar).

Preparation of 5,11,17,23,29,35-Hexabromo-37,38, 39,40,41,42-hexaacetoxycalix[6]arene (13)

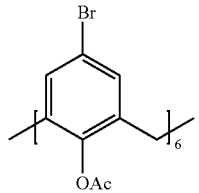

Starting from 8.62 g (7.81 mmol) of 12 and 5.77 g (70.29 mmol) of anhydrous sodium acetate in 100 ml of acetic anhydride, 9.24 g (87%) of 13 was obtained as a white solid.

Recrystallisation from m-xylene yielded X-ray quality single crystals, $13.2C_8H_{10}$, which were also submitted for microanalysis. m.p.>270° C. (dec.); IR (KBr) 2928 (w), 1764 (s), 1574 (w), 1450 (m), 1369 (m), 1211 (s), 1163 (s), 869 (m) cm$^{-1}$; $^1$H NMR (CDCl$_3$, 25° C., 500 MHz) δ 7.80-5.82 (m, 12H, ArH), 4.21-3.08 (m, 12H, ArCH2Ar), 2.61-1.66 (m, 18H, CH3); 13C NMR (CDCl$_3$, 25° C., 126 MHz) signals too broad; MS (ESI) m/z calcd for $(C_{54}H_{42}Br_6O_6+Na)+$ 1384.76, found 1384.70; elemental analysis Calcd (%) for $C_{54}H_{42}Br_6O_{12}+0.3C_8H_{10}$: C, 48.59, H, 3.25; found: C, 48.44; H, 3.47.

Crystal/refinement details for 3c. $2C_8H_{10}$: $C_{70}H_{62}Br_6O_{12}$, M=1574.66, F (000)=788 e, triclinic, P-1, Z=1, T=153(2) K, a=11.347(2), b=12.878(2), c=13.849(2)Å, α=112.802(2), β=98.427(2), γ=110.792(2)°, V=1646.6(5) Å$^3$, Dc=1.588 gcm$^{-3}$, $\mu_{Mo}$=3.719 mm$^{-1}$, sin θ/λmax=0.6605, N (unique)= 7632 (merged from 14667, $R_{int}$=0.0345, $R_{sig}$=0.0613), $N_o$ (I>2s(I))=5452, R=0.0488, wR2=0.1251 (A, B=0.077, 0), GOF=1.008, $|\Delta\rho_{max}|$=1.4(1) eÅ$^{-3}$. CCDC, 669057.

Preparation of 5,11,17,23,29,35-Hexa(diethoxyphosphoryl)-37,38,39,40,41,42-hexaacetoxycalix[6]arene (14)

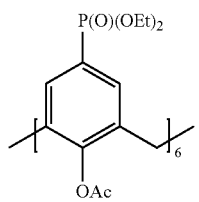

Starting from 3.00 g (2.21 mmol) of 13 in 30 ml of benzonitrile, 0.43 g (3.32 mmol) of NiCl$_2$ and 5.69 ml (33.19 mmol) of P(OEt)$_3$, 3.62 g (96%) of 14 was obtained as a light yellow solid. Recrystallisation from toluene yielded X-ray quality single crystals, $14.1/2C_7H_8.H_2O$, which were also submitted for microanalysis. R$_f$ 0.27 (1:4 methanol-ethyl acetate); m.p. 178-180° C.; IR (KBr) 2985 (m), 2911 (m), 1764 (s), 1643 (w), 1458 (m), 1372 (m), 1272 (m), 1020 (s), 966 (s), 795 (w), 605 (m) cm$^{-1}$; $^1$H NMR (CDCl$_3$, 25° C., 600 MHz) δ 7.52 (br s, 12H, ArH), 4.32-3.86 (m, 24H, POCH$_2$), 3.71 (br s, 12H, ArCH$_2$Ar), 1.98 (br s, 18H, CH3), 1.24 (m, 36H, POCH$_2$CH$_3$); $^{13}$C NMR (CDCl3, 25° C., 151 MHz) δ 167.86, 150.98, 132.92, 132.34, 126.67 (d, $^1J_{P-C}$=191.6 Hz), 62.25 (d, $^2J_{P-C}$=5.3 Hz), 31.22, 20.08, 16.25 (d, $^3J_{P-C}$=6.2 Hz); $^{31}$P NMR (CDCl$_3$, 25° C., 202 MHz) δ 17.75; MS (FAB) m/z calcd for $(C_{78}H_{102}O_{30}P_6+H)^+$ 1705, found 1705; elemental analysis Calcd (%) for $C_{78}H_{102}O_{30}P_6+0.85H_2O$: C, 54.44; H, 6.07; found: C, 54.31; H, 5.92. Crystal/refinement details for 3d. $1/2C_7H_8.H_2O$: $C_{81.5}H_{108}O_{31}P_6$, M=1769.50, F (000)=1870 e, triclinic, P-1, Z=2, T=153(2) K, a=15.701(2), b=15.946(2), c=20.010(2) Å, α=72.218(2), β=85.667(2), γ=80.292(2)°, V=4700.7(10) Å$^3$, Dc=1.250 gcm$^{-3}$, $\mu_{Mo}$=0.190 mm$^{-1}$, sin θ/λmax=0.6722, N (unique)= 21036 (merged from 34889, $R_{int}$=0.0201, $R_{sig}$=0.0411), $N_o$ (I>2σ(I))=13529, R=0.1346, wR2=0.2911 (A, B=0.05, 23.0), GOF=1.142, $|\Delta\rho_{max}|$=555 1.8(1) eÅ$^{-3}$. CCDC, 669058.

Preparation of 5,11,17,23,29,35-Hexa(diethoxyphosphoryl)-37,38,39,40,41,42-hexahydroxycalix[6]arene (15)

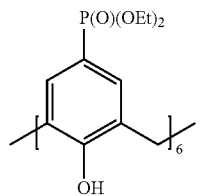

Starting from 3.60 g (2.21 mmol) of 14 and 1.78 g (31.68 mmol) of KOH in 80 ml of methanol, 80 ml of tetrahydrofuran and 80 ml of water, 3.05 g (99%) of 15 was obtained as a light yellow solid. Recrystallisation from ethyl acetate/hexane yielded a white solid suitable for microanalysis. m.p. 167-560 169° C.; IR (KBr) 3286 (br), 2983 (m), 2907 (m), 1597 (m), 1476 (m), 1393 (w), 1280 (m), 1023 (s), 966 (s), 796 (m) cm$^{-1}$; $^1$H NMR (CDCl$_3$, 25° C., 500 MHz) 610.49 (br s, 6H, OH), 7.66 (d, 12H, ArH, $J_{P-H}$=13.0 Hz), 4.20-3.72 (m, 36H, POCH$_2$ and ArCH$_2$Ar), 1.29 (t, 36H, POCH$_2$CH$_3$, J=7.0 Hz); 13C NMR (CDCl$_3$, 25° C., 126 MHz) δ 153.01, 133.82 (d, $^2J_{P-C}$=11.3 Hz), 126.91 (d, 3JP-C=16.3 Hz), 122.06 (d, $^1J_{P-C}$=193.7 Hz), 62.09 (d, $^2J_{P-C}$=5.6 Hz), 31.74, 16.31 (d, $^3J_{P-C}$=6.3 Hz); $^{31}$P NMR (CDCl$_3$, 25€C, 101 MHz) δ 18.87; MS (ESI) m/z calcd for $(C_{66}H_{90}O_{24}P_6+H)+$ 1453.43, found 1453.12; elemental analysis Calcd (%) $C_{66}H_{90}O_{24}P_6+$ 1.65H$_2$O: C, 53.45, H$_{6.34}$; found: C, 53.47; H, 6.36.

5,11,17,23,29,35-Hexa(dihydroxyphosphoryl)-37,38, 39,40,41,42-hexahydroxycalix[6]arene (16)

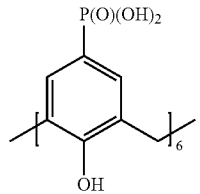

Starting from 6.61 ml (50.07 mmol) of bromotrimethylsilane and 3.03 g (2.09 mmol) of 15 in 80 ml of dry acetonitrile, 2.31 g (99%) of 16 was obtained as a white solid. Purification using the ion exchange resin, Dowex 50W yielded a white solid suitable for microanalysis. m.p.>280° C. (dec.); IR 570 (KBr) 3395 (br), 2300 (br), 1597 (m), 1476 (m), 1384 (m), 1279 (m), 1125 (s), 957 (m), 876 (m) cm$^{-1}$; $^1$H NMR (DMSO-d$_6$, 25° C., 500 MHz) δ 7.33 (br s, 12H, ArH), 5.51 (br s, COH/POH, shifts downfield with increasing [H]+), 3.85 (br s, 12H, ArCH$_2$Ar); $^{13}$C NMR (DMSO-d$_6$, 25° C., 126 MHz) δ 155.17, 131.36, 127.45, 123.48 (d, $^1J_{P-C}$=186.1 Hz), 31.08; $^{31}$P NMR (DMSO-d$_6$, 25° C., 101 MHz) δ 15.71; MS (ESI) m/z calcd for $(C_{42}H_{42}O_{24}P_6+H)+$ 1117.06, found 1117.28; elemental analysis Calcd (%) for $C_{42}H_{42}O_{24}P_6$+ 1.1$H_2O$: C, 44.39; H, 3.92; found: C, 44.10; H, 3.60.

Example 4

Preparation of Phosphonated Calix[8]Arene

Preparation of 5,11,17,23,29,35,41,47-Octabromo-49,50,51,52,53,54,55,56-octahydroxycalix[8]arene (17)

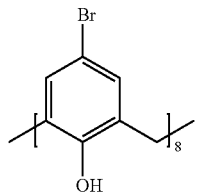

Starting from 7.25 ml (0.14 mmol) of bromine in 100 ml of DMF and 10.00 g (11.79 mmol) of calix[8]arene in 400 ml of DMF, 16.99 g (98%) of 17 was obtained as a light orange solid. $^1$H NMR (DMSO-$d_6$, 25° C., 300 MHz) δ 8.92 (br s, 8H, OH), 6.99 (s, 16H, ArH), 3.86 (s, 16H, ArCH$_2$Ar).

Preparation of 5,11,17,23,29,35,41,47-Octabromo-49,50,51,52,53,54,55,56-octaacetoxycalix[8]arene (18)

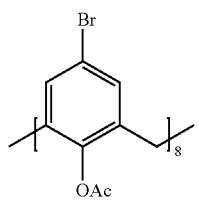

Starting from 8.00 g (5.44 mmol) of 17 and 5.35 g (65.23 mmol) of anhydrous sodium acetate in 80 ml of acetic anhydride, 7.19 g (73%) of 18 was obtained as a light green solid. $^1$H NMR (DMSO-$d_6$, 25° C., 300 MHz) δ 7.22 (s, 16H, ArH), 3.60 (s, 16H, ArCH$_2$Ar), 2.00 (s, 24H, CH$_3$).

Preparation of 5,11,17,23,29,35,41,47-Octa(diethoxyphosphoryl)-49,50,51,52,53,54,55,56-octaacetoxycalix[8]arene (19)

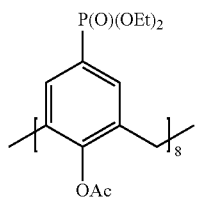

Starting from 2.00 g (1.11 mmol) of 18 in 40 ml of benzonitrile (not completely soluble), 0.29 g (2.21 mmol) of NiCl$_2$ and 3.79 ml (22.13 mmol) of P(OEt)$_3$, 2.43 g (97%) of 19 was obtained as a light yellow solid. Recrystallisation from ethyl acetate/dichloromethane yielded X-ray quality single crystals, 19, which were also submitted for microanalysis. R$_f$ 0.12 (1:4 methanol-ethyl acetate); m.p. 223-225° C.; IR (KBr) 2984 (m), 2911 (m), 1766 (s), 1653 (w), 1460 (m), 1372 (m), 1273 (m), 1020 (s), 966 (s), 795 (w), 621 (m) cm$^{-1}$; $^1$H NMR (CDCl$_3$, 25°, 500 MHz) δ 7.44 (d, 16H, ArH, J$_{P-H}$=13.5 Hz), 4.16-3.90 (m, 32H, POCH$_2$), 3.67 (s, 16H, ArCH$_2$Ar), 1.89 (s, 24H, CH$_3$), 1.25 (t, 48H, POCH$_2$CH$_3$, J=7.0 Hz); $^{13}$C NMR (CDCl$_3$, 25° C., 126 MHz) δ 167.78, 150.93, 132.97 (d, $^2$J$_{P-C}$=10.1 Hz), 132.37 (d, $^3$J$_{P-C}$=15.1 Hz), 126.67 (d, $^1$J$_{P-C}$=189.9 Hz), 62.27 (d, $^2$J$_{P-C}$=5.0 Hz), 31.93, 19.95, 16.25 (d, $^3$J$_{P-C}$=6.3 Hz); $^{31}$P NMR (CDCl$_3$, 25° C., 101 MHz) δ 17.73; MS (ESI) m/z calcd for ($C_{104}H_{136}O_{40}P_8$+H)+ 2273.66, found 2273.26; elemental analysis Calcd (%) for $C_{104}H_{136}O_{40}P_8$+1.85$H_2O$: C, 54.14; H, 6.10; found: C, 54.06; H, 6.01. Crystal/refinement details for 4d: $C_{104}H_{136}O_{40}P_8$, M=2273.89, F (000)=1200 e, triclinic, P-1, Z=1, T=100(2) K, a=14.055(2), b=14.498(2), c=15.077(2) Å, α=75.011(3), β=88.677(3), γ=74.754(3)°, V=2859.9(7) Å$^3$, Dc=1.320 gcm$^{-3}$, μ$_{Mo}$ 595=0.205 mm$^{-1}$, sin θ/λmax=0.6240, N (unique)=12270 (merged from 20387, R$_{int}$=0.0214, R$_{sig}$=0.0415), N$_o$ (I>2σ(I))=8474, R=0.0985, wR2=0.2717 (A, B=0.17, 4.66), GOF=1.050, |Δρ$_{max}$|=1.4(1) eÅ$^{-3}$. CCDC, 669059.

Preparation of 5,11,17,23,29,35,41,47-Octa(diethoxyphosphoryl)-49,50,51,52,53,54,55,56-octahydroxycalix[8]arene (20)

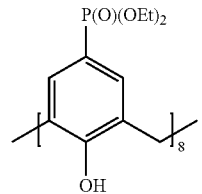

Starting from 2.40 g (1.06 mmol) of 19 and 1.19 g (21.14 mmol) of KOH in 50 ml of methanol, 50 ml of tetrahydrofuran and 50 ml of water, 2.00 g (98%) of 20 was obtained as a light yellow solid. Recrystallisation from ethyl acetate/ dichloromethane yielded a white solid suitable for microanalysis. m.p. 183-185° C.; IR (KBr) 3274 (br), 2983 (m), 2905 (m), 1597 (m), 1476 (m), 1393 (m), 1279 (m), 1022 (s), 968 (s), 795 (m) cm$^{-1}$; $^1$H NMR (CDCl$_3$, 25° C., 500 MHz) δ 9.56 (br s, 8H, OH), 7.66 (d, 16H, ArH, J$_{P-H}$=13.5 Hz), 4.62-3.32 (m, 48H, ArCH$_2$Ar and POCH$_2$), 1.27 (t, 48H, POCH$_2$CH$_3$, J=7.0 Hz); $^{13}$C NMR (CDCl$_3$, 25° C., 126 MHz) δ 152.39, 133.07 (d, $^2$J$_{P-C}$=10.1 Hz), 128.37 (d, $^3$J$_{P-C}$=15.1 Hz), 122.45 (d, $^1$J$_{P-C}$=191.2 Hz), 62.14 (d, $^2$J$_{P-C}$=5.0 Hz), 31.12, 16.32 (d, $^3$J$_{P-C}$=6.3 Hz); $^{31}$P NMR (CDCl$_3$, 25°, 101 MHz) 618.65; MS (ESI) m/z calcd for ($C_{88}H_{120}O_{32}P_8$−H)− 1935.56, found 1935.36; elemental analysis Calcd (%) for $C_{88}H_{120}O_{32}P_8$+1.6$H_2O$: C, 53.75; H, 6.31; found: C, 53.48; H, 6.03.

Preparation of 5,11,17,23,29,35,41,47-Octa(dihydroxyphosphoryl)-49,50,51,52,53,54,55,56-octahydroxycalix[8]arene (21)

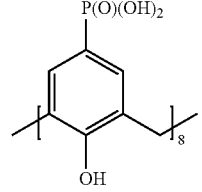

Starting from 0.69 ml (5.22 mmol) of bromotrimethylsilane and 0.32 g (0.16 mmol) of 20 in 20 ml of dry acetonitrile, 0.24 g (99%) of 21 was obtained as a white solid. Purification using the ion exchange resin, Dowex 50W yielded a white solid suitable for microanalysis. m.p.>280° C. (dec.); IR (KBr) 3241 (br), 2300 (br), 1599 (m), 1480 (m), 1384 (m), 1279 (m), 1125 (s), 963 (s), 877 (m) cm-1; $^1$H NMR (DMSO-$d_6$, 25° C., 500 MHz) δ 7.20 (d, 16H, ArH, $J_{P-H}$=12.0 Hz), 5.08 (br s, COH/POH, shifts downfield with increasing [H]+), 3.94 (s, 16H, ArCH$_2$Ar); $^{13}$C NMR (DMSO-$d_6$, 25° C., 126 MHz) δ 155.21, 130.95, 126.95, 123.25 (d, $^1J_{P-C}$=189.9 Hz), 30.38; $^{31}$P NMR (DMSO-$d_6$, 25° C., 101 MHz) δ 16.54; MS (ESI) m/z calcd for $(C_{56}H_{56}O_{32}P_8+H)$+ 1489.07, found 1489.02; elemental analysis Calcd (%) for $C_{56}H_{56}O_{32}P_8$+ 1.2H$_2$O: C, 44.53; H, 3.90; found: C, 44.19; H, 3.54.

Example 5

Alternate process for preparation of p-Phosphonato-calix[n]arenes

Compounds 2 and 3 were prepared by modified literature procedures.[1]

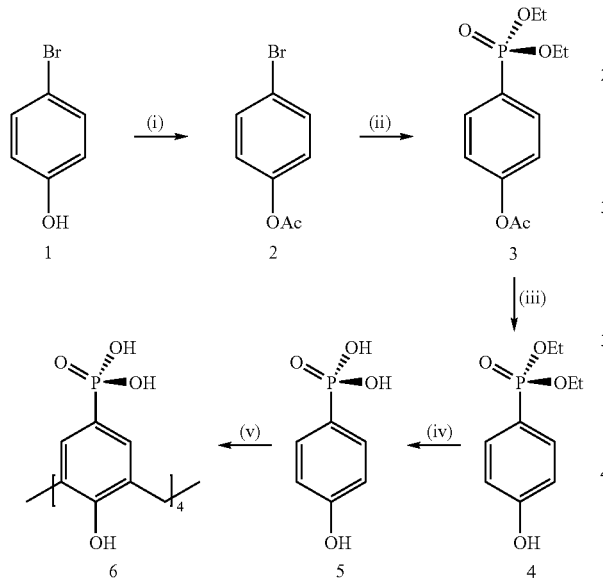

H$_2$O (iv) Me$_3$SiBr/MeCN (v) CH$_2$O/PO$_4$H$_3$. Ac=acetyl, Et=ethyl, Me=methyl, THF=tetrahydrofuran.

Preparation of p-Bromophenylacetate (22)[1]

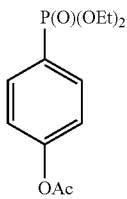

A mixture of 30.00 g (0.17 mol) of p-bromophenol and 14.22 g (0.17 mol) of anhydrous sodium acetate in 100 ml of acetic anhydride was refluxed for 1 hour. After cooling to RT the solution was slowly quenched with 300 ml of water. The oil formed was dissolved in 150 ml of DCM and separated from the aqueous phase. The organic layer was washed with water (3×30 ml), dried over MgSO$_4$ and evaporated under reduced pressure to leave a light orange oil. The oil was purified by distillation under reduced pressure to yield 35.37 g (95%) of 22 as a colourless oil. The $^1$H NMR spectrum was in agreement with the reported literature.

Preparation of p-Diethoxyphosphorylphenylacetate (23)[1]

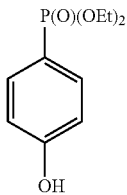

25.61 ml (0.15 mol) of triethyl phosphite was added dropwise to a suspension of 0.81 g (6.22 mmol) of anhydrous NiCl$_2$ and 26.76 g (0.12 mol) of 22 at 180° C. The solution was stirred for 0.5 hours and cooled to RT. The dark orange oil was purified by distillation under reduced pressure to yield 23.74 g (70%) of 23 as a colourless oil. The $^1$H NMR spectrum was in agreement with the reported literature.

Preparation of p-Diethoxyphosphorylphenol (24)

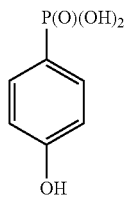

A mixture of 12.02 g (44.17 mmol) of 23 and 4.96 g (88.33 mmol) of KOH in 50 ml of methanol, 50 ml of tetrahydrofuran and 50 ml of water was stirred for 2 hours at RT. The solvents were removed under reduced pressure and the resulting oil treated with 100 ml of DCM and 100 ml of 2N HCl. The organic layer was separated, washed with 2N HCl (1×30 ml), water (2×30 ml), dried over MgSO$_4$ and evaporated under reduced pressure to yield 9.83 g (97%) of 24 as a colourless oil. $^1$H NMR (CDCl$_3$, 25° C., 600 MHz) δ 7.66-7.60 (m, 2H, ArH), 7.02-6.97 (m, 2H, ArH), 4.14-4.01 (m, 4H, POCH$_2$), 1.30 (dt, 6H, CH$_3$, J=6.0/0.6 Hz); $^{13}$C NMR (CDCl$_3$, 25° C., 151 MHz) δ 161.72 (d, $^4J_{P-C}$=3.5 Hz), 133.74 (d, $^2J_{P-C}$=11.6 Hz), 115.97 (d, $^3J_{P-C}$=16.4 Hz), 115.65 (d, $^1J_{P-C}$=197.4 Hz), 62.32 (d, $^2J_{P-C}$=5.3 Hz), 16.19 (d, $^3J_{P-C}$=6.5 Hz); $^{31}$P NMR (CDCl$_3$, 25° C., 243 MHz) δ 20.66.

p-Dihydroxyphosphorylphenol (25)

Bromotrimethylsilane (1 ml) was added to 24 (0.5 g) in dry acetonitrile (10 ml) and the solution was refluxed for 24 h. The volatiles were removed under reduced pressure and acetonitrile (20 ml) was added to the residue and the solution stirred for 1 hour. The volatiles were removed under reduced pressure to yield 25 in quantitative yield, which was used without further purification in the next step. $^1$H NMR (DMSO-$d_6$, 25° C., 500 MHz) δ 8.6 (br s, 3H, COH/POH), 7.49 (dd, 2H, ArH, J=12.5/8.5 Hz), 6.81 (dd, 2H, ArH, J=8.5/3.0 Hz); $^{13}$C NMR (DMSO-$d_6$, 25° C., 126 MHz) δ 159.82 (d, $^4J_{P-C}$=3.3 Hz), 132.52 (d, $^2J_{P-C}$=11.3 Hz), 123.47 (d, $^1J_{P-C}$=189.4 Hz), 114.92 (d, $^3J_{P-C}$=15.3 Hz); $^{31}$P NMR (DMSO-$d_6$, 25° C., 243 MHz) δ 14.69. Crystal/refinement details for 25a: $C_{10}H_{15}O_4P$, M=230.19, F (000)=488 e, monoclinic, P2$_1$/n (No. 14), Z=4, T=100(2) K, a=8.5520(3), b=15.5263(4), c=8.6384(2) Å, β=92.433(2)°, V=1145.98(6) Å$^3$, $D_c$=1.334 gcm$^{-3}$, $\mu_{Mo}$=0.232 mm$^{-1}$, sin θ/$\lambda_{max}$=0.7035, N (unique)=3340 (merged from 13120, $R_{int}$=0.0303, $R_{sig}$=0.0306), $N_o$ (I>2σ(I))=2694, R=0.0350, wR2=0.0948 (A, B=0.06, 0.1), GOF=1.003, |Δρ$_{max}$|=0.41(6) e Å$^{-3}$.

Preparation of p-phosphonato-calix[n]arenes

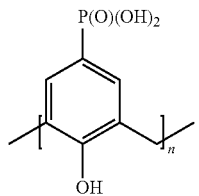

The procedure attempted consisting of heating a mixture of p-dihydroxyphosphorylphenol (1 g), formalin (10 ml) and phosphoric acid (1 ml) at 80-85° C. prior increasing rapidly the temperature to 110-120° C. and the reaction mixture was held to this temperature for 2 hours till a yellowish resin is formed. Work up procedure was performed by adding acetonitrile effecting the precipitation of p-phosphonato-calix[n]arenes (60% yield). The $^1$H NMR spectrum was in agreement with the reported literature of such compounds.[2,3]

Alternative condensations reactions for the synthesis of p-phosphonato-calix[n]arenes the involving other acid catalysts include but not limited to, the mineral acids hydrofluoric acid, hydrochloric acid, sulphuric acid, nitric acid and boric acid and organic acids such as acetic acid, formic acid, citric acid and oxalic acid.

Alternative reactions involving base catalysts include but not limited to the alkali metal hydroxides such as potassium hydroxide, barium hydroxide, caesium hydroxide, sodium hydroxide, strontium hydroxide, calcium hydroxide, lithium hydroxide and rubidium hydroxide. Also ammonia, pyridine, alkyl amines and imidazoles.

Example 6 p-Phosphonic acid calix[4]arene is moderately soluble in dimethyl sulfoxide (DMSO), slightly soluble in cold water, and alcohols such as methanol and insoluble in all other common organic solvents. Referring to FIG. 2, slow evaporation of a saturated solution of p-phosphonic acid calix[4] arene in methanol/6N HNO$_3$/Cu(NO$_3$)$_2$ or water/curcumin afforded colourless single crystals suitable for X-ray diffraction studies, 1a and 1b respectively (19). Copper cations are not incorporated into the structure, 1a, but their presence are necessary to effect crystallization. Changing the cation to rubidium, cesium or nickel also gave colourless single crystals with the same unit cell dimensions and thus are also devoid of metal ions. The overall structure, 1a, is a compact bilayer arrangement with the bilayers linked together by hydrogen bonding between phosphonic acid groups from different bilayers. Crystallization from water in the presence of curcumin afforded structure 1b. Changing curcumin to other organic molecules such as -carotene or carborane also yielded colourless crystals with the same unit cell dimensions (20). In the absence of such organic molecules it was not possible to crystallize p-phosphonic acid calix[4]arene from water. The structure of 1b is very similar to that of 1a, taking on the same bilayer arrangement, albeit now with the bilayers separated by a layer of water molecules, FIGS. 2 (A and B).

Both structures crystallize in the same tetragonal space group P4/n, the major difference in cell dimensions being associated with the tetragonal c axis, 11.067(3) and 14.0678 (8) Å for 1a and 1b respectively. The tetragonal axis is normal to the bilayers with the cone shaped calix[4]arenes residing on four fold symmetry axes, and thus the difference in c is associated with the incorporation of a layer of water molecules for 1b relative to 1a. The a (and b) axes for the two structures are very similar (12.130(4) and 11.938(6) Å, 1a and 1b respectively), which reflects the similarity in packing within the bilayers in the two structures. In 1a there is inclusion of a disordered methanol molecule in the cavity of the calixarenes with the methyl group directed towards the cavity. Similarly, in structure 1b the cavity of each calixarene takes up a disordered water molecule. In both structures the calixarene adopts a crystallographically imposed symmetrical cone conformation. This contrasts with a partially pinched cone conformation containing an ordered water molecule in the cavity of sulfonated calixarene, which involves O—H . . . π interactions (21). In both structures the phenolic hydroxyl groups at the lower rim of the calixarene are engaged in a circular hydrogen bonded network equally disordered in opposite directions (O—H . . . O distance, 1.82 and 1.83 Å for 1a and 1b respectively).

The bilayer arrangements in both structures have calixarenes orientated in opposite directions, FIGS. 2 (A and B). Both bilayers involve intricate hydrogen bonding networks formed by bridging methanol or water molecules between phosphonic acid moieties within each bilayer (O—H . . . OCH$_3$ distances, 1.78-2.05 Å for 1a and O—H . . . OH$_2$ distances, 1.67-1.95 Å for 1b), FIGS. 2 (C and D). In addition methanol and water embedded in the cavity of both structures interacts with the inner walls of the calixarene via CH or OH . . . interactions (short contacts for HOC . . . centroid and H$_2$O . . . centroid are 4.01 Å and 4.08 Å, 1a and 1b respectively). The closest distance between phosphorus atoms of neighbouring bilayers is 4.62 Å in 1a whereas it is 6.20 Å in 1b where there is no hydrogen bonding between phosphonic acid groups across different bilayers. In 1a the phosphonic acids are engaged in a complex hydrogen bonding array forming a compact bilayer with short contact —POH . . . O=P(OH)$_2$ of 1.61-1.75 Å whereas in 1b water molecules in the hydrophilic layer are interposed between bilayers with OH$_2$ . . . O=P (OH)$_2$ 1.88-1.95 and H$_2$O . . . HOPO(OH) distances ranging from 1.88-2.23 Å, FIGS. 2 (C and D). A subtle difference in the packing of calixarenes within the bilayers is that in 1a two methylene protons from a single carbon atom of one calixarene reside close to the face of an aromatic ring of another calixarene, CH$_2$ . . . π interplay, whereas in 1b only one of the H-atoms from the same methylene group is associated with such interaction.

Example 7

Crystallization of p-phosphonic acid calix[4]arene is also possible using SDP involving a 1 M sodium hydroxide solution containing p-phosphonic acid calix[4]arene as the corresponding phosphonate and a HCl solution at different concentrations (1.0 M, 1.5 M, 3.0 M, 6.0 M). The experiment consisted of injecting the alkaline solution of p-phosphonic acid calix[4]arene in one feed jet, and a solution of HCl in the other feed jet at room temperature (1 ml/s, grooved disc, 1500 rpm disc rotation) to ensure an acidic solution upon mixing. The spinning disc process induces rapid crystallization and is dependent on the molarity of the acid used, and generally yields micron size particles. However using HCl solutions containing 10% acetonitrile results in the formation of specifically 3.0(3) or 20(2) nm particle (Dynamic Light Scattering) depending on the concentration of the acid, FIG. 3; the ability to fabricate nano-particles of a specific size, and stabilized by acetonitrile, under process intensification is noteworthy.

In the absence of acetonitrile, increasing concentrations of HCl induces immediate formation of micron size particles which then re-disperse to form smaller particles upon standing for a few hours, notably 3.0(3) nm for 3 M HCl and 20(2) nm for 1.0 M HCl. The presence of acetonitrile circumvents the formation of micron size particles, affording stable 3.0(3) and 20(2) nm particles, 3.0 M HCl and 1.0 M HCl respectively, FIG. 3. Moreover, the particle size can also be controlled by varying the speed of the disc, amongst other parameters, for example, at 2000 rpm disc speed, 80(7) nm particles are formed for 1 M HCl, and the use of acetonitrile as a stabilizing agent/surfactant in conjunction with SDP is critical (Supplementary Information). Acetonitrile was selected for this purpose because of its ability to bind in the cavity of the calixarene on the surface of the nano-particles with the polar group directed to solution space in the same way as methanol does in 1a.(25)

The X-ray powder diffraction (XRPD) pattern for the as synthesized, Scheme 1, compound p-phosphonic acid calix[4]arene matches the predicted powder pattern for the aforementioned structure 1a (22), FIG. 4. Analysis of the peak widths using the Scherrer equation gave a particle size, 16-30 nm, which is comparable to that of the 20(2) nm particles formed by SDP. Precipitation of an aqueous solution of p-phosphonic acid calix[4]arene with excess concentrated HCl produced a solid with the same crystal packing as the as synthesized compound p-phosphonic acid calix[4]arene. Thus the packing of the calixarenes in the as synthesized product is similar to the compact bilayer as seen for structure 1a. Removal of the solvent for the above prepared 3.0(3) nm particles (without acetonitrile) gave a diffraction pattern with a dominant peak at 2 9.0° which equates to a d spacing of 1.0 nm, and matches closely the bilayer spacing in the compact bilayer, 1a, FIG. 4F.

The nano-raft assemblies also show remarkable stability in DMSO at room temperature, contrary to the fact that DMSO is effectively competing for hydrogen bond formation with the calixarene. Calixarene dimers have been shown to "denature" within seconds of addition of a few % of DMSO, which disrupts the hydrogen bonded array holding the dimer together (23). Thus our present system is intriguing as the nano-rafts slowly dissociate over the course of 36 hours into solvated monomeric units, FIG. 5. A fresh deuterated DMSO solution of p-phosphonic acid calix[4]arene gives a series of doublets for the two equivalent aromatic protons split by the single phosphorus environment in the $^1$H NMR spectrum. Over time the monomer doublet becomes dominant as DMSO breaks up the nano-rafts. This is confirmed by $^{31}$P NMR showing a series of multiplets around 7 and 14 ppm which converge to a singlet at 14.7 ppm for the monomeric unit. The formation of nano-rafts does not depend on the concentration or pH of the solution but surprisingly its formation is sensitive to the presence of trace amounts of acetonitrile. One plausible explanation for this observation is that the residual acetonitrile in the as synthesized solid is orchestrating the nano-rafts assembly. Acetonitrile has been shown to form a variety of hydrogen bonds with phenol in solution (24), inclusion complexes with calixarenes (25) and as surfactant stabilizers. Dynamic solution studies were attempted to establish the size of the nano-rafts via $^{31}$P diffusion ordered spectroscopy (DOSY), however due to the slow diffusing nature of the calixarene in DMSO the technique was not suitable. p-phosphonic acid calix[4]arene has solubility limitations with the exception of protic solvents where nano-rafts are not evident.

MALDI-TOF mass spectrometry on p-phosphonic acid calix[4]arene gave further evidence for the compact bilayer packing in the solid state, showing fragmentation of the bilayer devoid of solvent, FIG. 6. The nano-rafts were observed only when using an acidic matrix such as dihydroxybenzoic acid (DHB) and successive peaks out to the 20-mer were obtained. This is consistent with fragments of the continuous structure in complex 1a being generated in the gas phase by the laser. These nano-rafts can be viewed as fragments of the bilayers with aggregates of 4 and 6 molecules of p-phosphonic acid calix[4]arene showing particular stability. Attempts at detecting larger fragments by increasing the extraction delay time and decreasing the laser power, were to no avail. These results are confirmed by ESI mass spectrometry in water or methanol showing aggregates of up to 8 molecules, also with no sign of associated solvent molecules, FIG. 7. The nature of the structure of 1a rules out the likelihood of formation of spheroidal arrays of calixarenes such as the Platonic and Archimedean solids, found in the p-sulfonato-calix[4]arene arrays of 12 calixarenes with all the cavities pointing away from the core of the arrays (6-8). In addition there are no magic number signals in the mass spectrum corresponding to such structures. There is no evidence for the formation of nano-arrays of the water containing complex 1b in the gas phase.

Example 8

Toxicity tests on p-phosphonato-calix[n]arenes detergents carried out at the Medical Research Council of the Royal Perth Hospital The tests were performed on two cell cultures Hella and Jurkat. The prepared culture cells have an estimated concentration of $6 \times 10^6$ cells/ml (50 µl of the stock solution was used in each well). The tests were carried out in a 96 well plates in triplicate for phosphonato-calix[n]arenes (n=4 and 5) using two different cell cultures, Jurkat and Hella cell lines. The results showed no toxicity up to 25 µg/ml and some minor cell death at higher concentration at 1 mg/ml.

Example 9

Cytotoxicity of p-phosphonated calixarenes

Cytotoxicity of these calixarenes were conducted using Peripheral Blood Mononucleus Cell line (PBMC) which were extracted from subjects blood (50 ml sample). Each calixarene compound was tested on three subjects out of a pool of 5 people (all caucasian females of 20-25 years of age). The extracted cell content represent 1% of the blood sample and comprised of Lymphocyte (60%) and monocytes (10-15%). The experiment was conducted by incubating the cells in a 96 well plate in triplicate with the calixarenes for 24 hours at different concentrations at an estimated concentration of 100000 cells per well.

Method

A pipeline was designed to obtain reliable preliminary toxicology data in vitro. The pipeline was designed to allow testing of any particles of interest within a short time frame. Peripheral blood mononuclear cells (PBMC) were chosen over other types of cells and cell lines because the calixarenes are meant to be injected into the body. PBMC provide more reliable data over other types of cells as H is a component of whole blood.

Harvesting of PBMC

PBMC were harvested using the Ficoll method. Fresh whole blood was collected from selected individuals in heparin tubes and the samples were processed within an hour of collection. The heparin tubes were centrifuged at 700G for 10 minutes and the buffy-coat from the tubes were extracted from the samples. Ficoll is carefully added to the bottom of the tube and the tube is spun at 700G for 20 minutes. PBMC floating on top of the Ficoll layer is then collected and washed twice by centrifuging the cells with RPMI at 400G for 8 minutes. The cells are then suspended in freezing media (10% DMSO in HIFCS) at 10 million cells per ml and stored as 1 ml aliquots in liquid nitrogen until it is ready for use.

Sterilization of Phosphonated Calixarenes

The phosphonated calixarenes were tested for their sterility prior being used to conduct experiments. 100 μL of each of the phosphonated calixarenes were seeded into blood agar plates and incubated for 1 week at 37° C. and 5% $CO_2$. Meanwhile, the samples were sterilized and 100 μl of the sterilized samples were then seeded into blood agar plates and incubated for 1 week at the same conditions. The preferred method of sterilization is microfiltration through a 0.2 μM Supor® membrane. All four calixarenes samples were sterilized using this method.

If filter sterilization is not successful, the alternate method was used which is autoclaving.

Cell Viability Assay (MTS Assay)

CellTitre 96© Aqueous One Solution Cell Proliferation Assay was used to measure cell viability. This assay kit is a colourimetric assay that uses a tetrazolium compound known as MTS that is bio-reduced due to mitochondrial activity in cell, producing formazan that is proportional to the number of viable cells. It was chosen over other cell viability assays such as CellGlo® or MTT assay to provide quick, simple, relatively reliable and relatively inexpensive method to acquire preliminary data on the toxicology of the phosphonated calixarenes. 10 μL of each sample (comprising 1 mM calixarene) were first added to the first 2 columns of the 96 well plate. A one in two serial dilution was performed from column 2 to column 11 across the 96 well plate leaving 10 μL of samples in each well. 100 μL of 100,000 cells in culture medium (10% HIFCS in RPMI) was added into each well followed by 5 μL of 1 in 10 phytohaemagglutinin (PHA) or 5 μL of 1× phosphate buffered saline (PBS) to respective wells. The PHA was added to trigger activation of lymphocytes which was hypothesised that it may alter the reading of the MTS assay. The plate was then incubated for 22 hours at 37° C. and 5% $CO_2$ before 20 μL of the MTS reagent was added to each wells. The plate is further incubated for another 4 hours and is read through a spectrophotometer at 490 nm. This assay was done in triplicate using PBMC from different individuals to account for variability in immune response.

Flow Cytometry

A 5 colour flow cytometry based assay was done to complement the MTS assay to provide a better snapshot of the toxicology profile of the calixarenes. Four concentrations from the MTS assay graph results (Control, 1, 1/4 dilution and 1/32 dilution) were chosen to illustrate the differences in cell profiles after the exposure of the calixarenes. 500,000 cells in 0.5 ml was cultured with 50 μL of calixarenes in polypropylene tubes (BD Falcon, Sarstedt) for 24 hours at 37° C., 5% $CO_2$, 10° angle with the lid loosely closed. Polypropylene tube cultures were chosen as it provides better yield of monocytes.

After the 24 hour incubation, a cell count was performed to ensure there were at least 200,000 cells in each sample. The cells were centrifuged at 400G for 8 minutes and washed twice with flow buffer (10% bovine serum albumin in 1×PBS) by centrifugation at 400G for 8 minutes. An antibody cocktail of 10 μL annexin V FITC (marker used to detect apoptosis of cells), 5 μL CD3 APC (marker for detection of T-cells), 2.5 μL CD14 PECy7 (marker for detection of monocytes), 5 μL HLA-DR PE (marker for detection of cell activation) and 5 μL 7-AAD (marker to detect cell death) in each tube was prepared. The cells were resuspended in 200 μL of 1× Annexin V binding buffer. 100 μL of the resuspended cells were added to flow tubes containing the antibody cocktail and was incubated at room temperature in the dark for at least 15 minutes. The samples were then read using BD FACS Canto flow cytometer within an hour of antibody incubation. The experiment was replicated in triplicates using PBMC from different individuals.

Calix[4]Arene

Figure 8A:
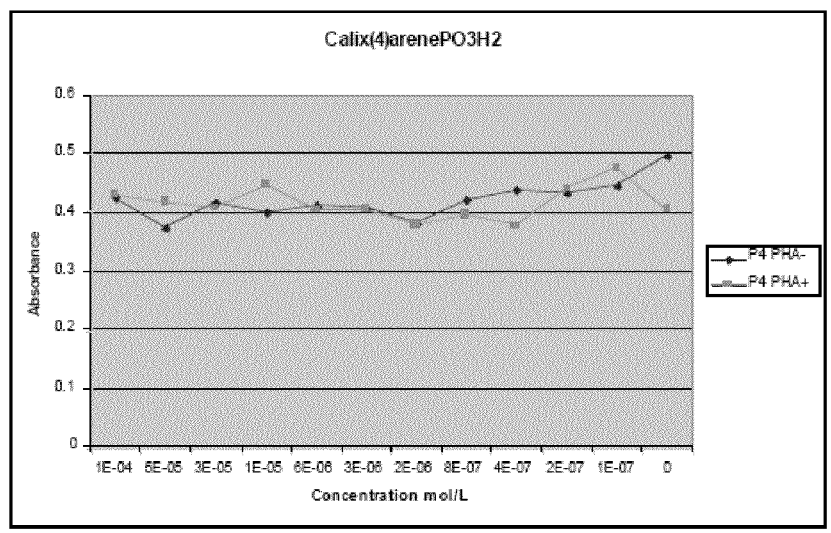
FIG. 8 is a graph showing cell viability over a range of concentrations of phosphonated calix[4]arene in two fold dilutions starting from $10^{-4}$M. The higher the absorbance reading shown on the vertical axis, the greater the cell viability. From this graph, it seems that there is no significant sign of toxicity with this calixarene.
Figure 8B:
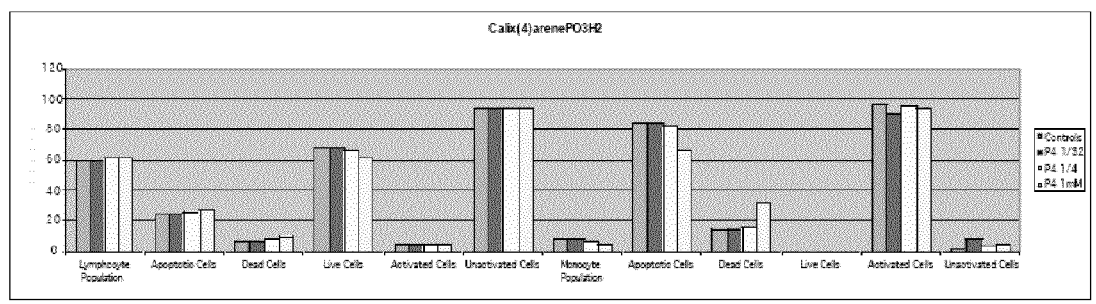

Phosphonated calix[4]arene was tested with flow cytometry at the following concentrations; 10-4M, 2.5×10-5M (1 in 4 dilution) and 3.13×10-6M (1 in 32 dilution). Lymphocyte and monocyte population characteristics are summarised in the graph in FIG. 8. Lymphocyte and monocyte population numbers are based on total population while apoptotic cells, dead cells, live cells etc are based on their respective populations. Lymphocytes normally make up 60% of total population. The proportion of dead lymphocytes seems to decline as the concentration of phosphonated calix[4]arene increases. However, this is most likely due to total lysis of cells, which cannot be detected by dead cell marker. Monocytes normally make up 10-15% of total population. The culturing process seems to cause most monocytes to be apoptotic due to their fragile nature. There is a slight decline in monocyte numbers with increasing concentration of this calixarene.

Calix[5]Arene

Figure 9A:
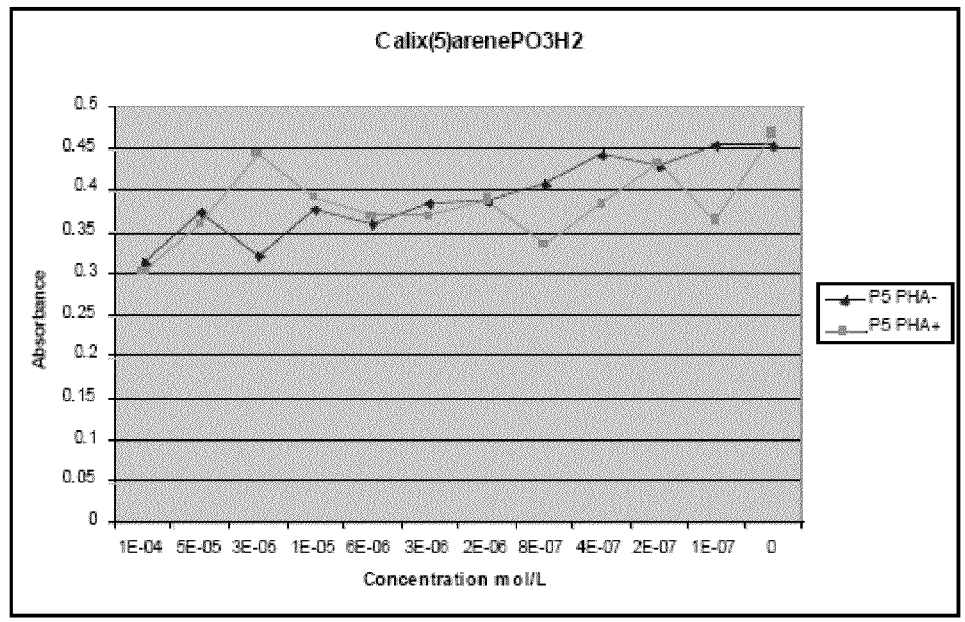
FIG. 9 is a graph showing cell viability over a range of concentrations of phosphonated calix[5]arene in two fold dilutions starting from $10^{-4}$M. The higher the absorbance reading shown on the vertical axis, the greater the cell viability. From this graph, it seems that there is less toxicity with this calixarene than with sulphonated calixarenes.
Figure 9B:
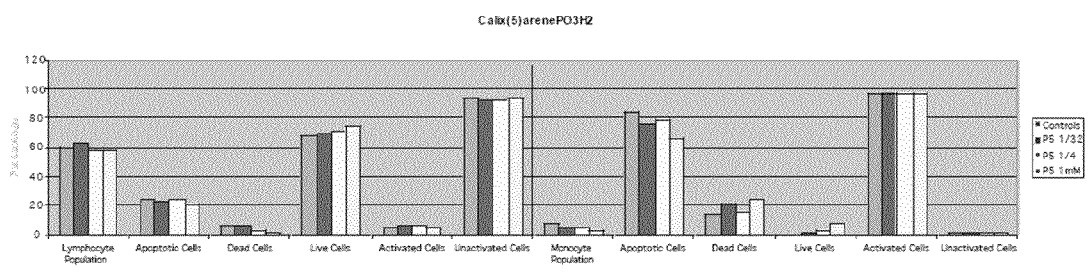
Figure 10:
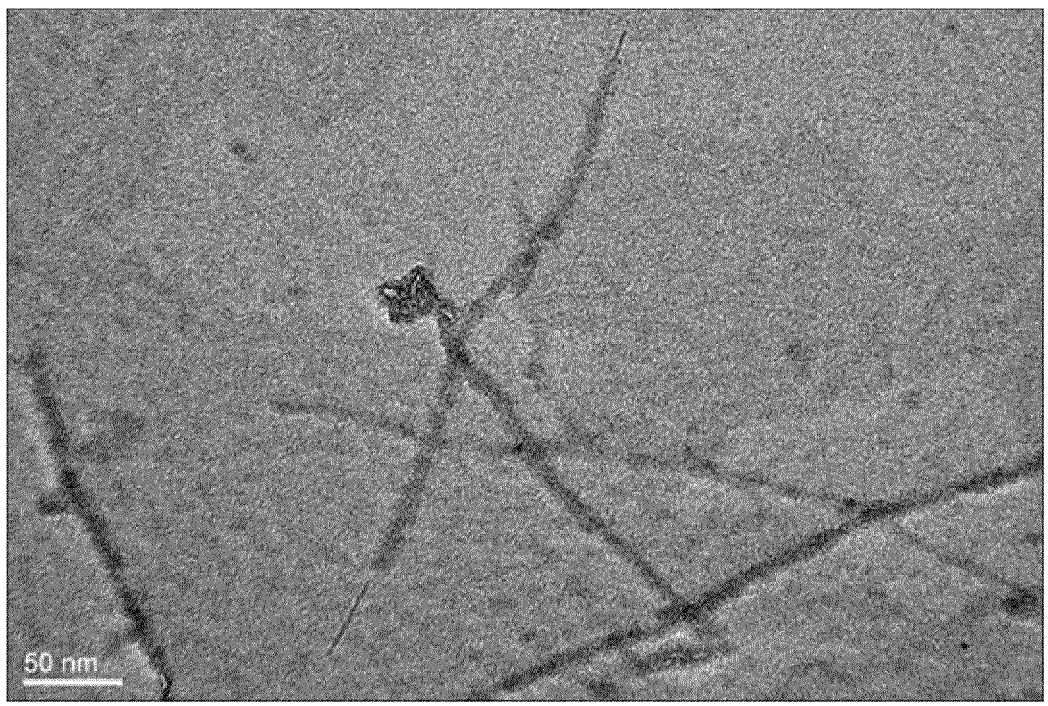
FIG. 10 is an image showing single-walled carbon nanotubes (SWCNTs) that have been successfully water solubilised using p-phosphonated calyx[n]arenes (n=5) and display a surface coating.
Figure 11:
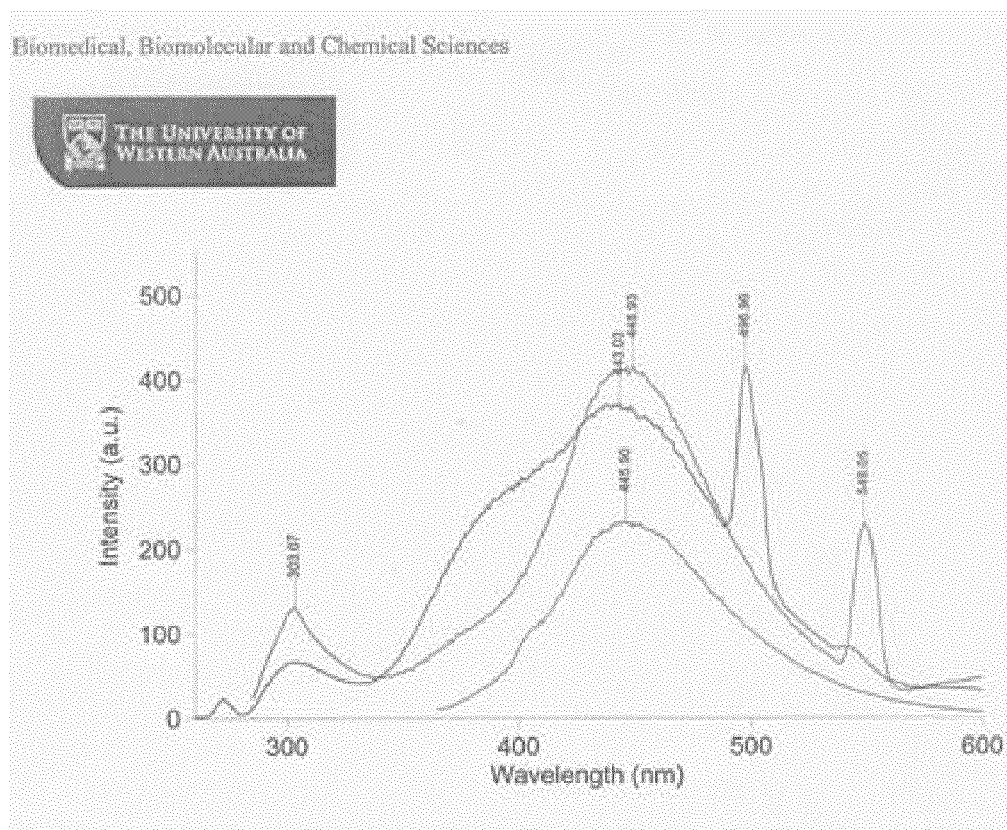
FIG. 11 is a spectrum showing the fluorescence of p-phosphonated calyx[5]arene.
Figure 12:
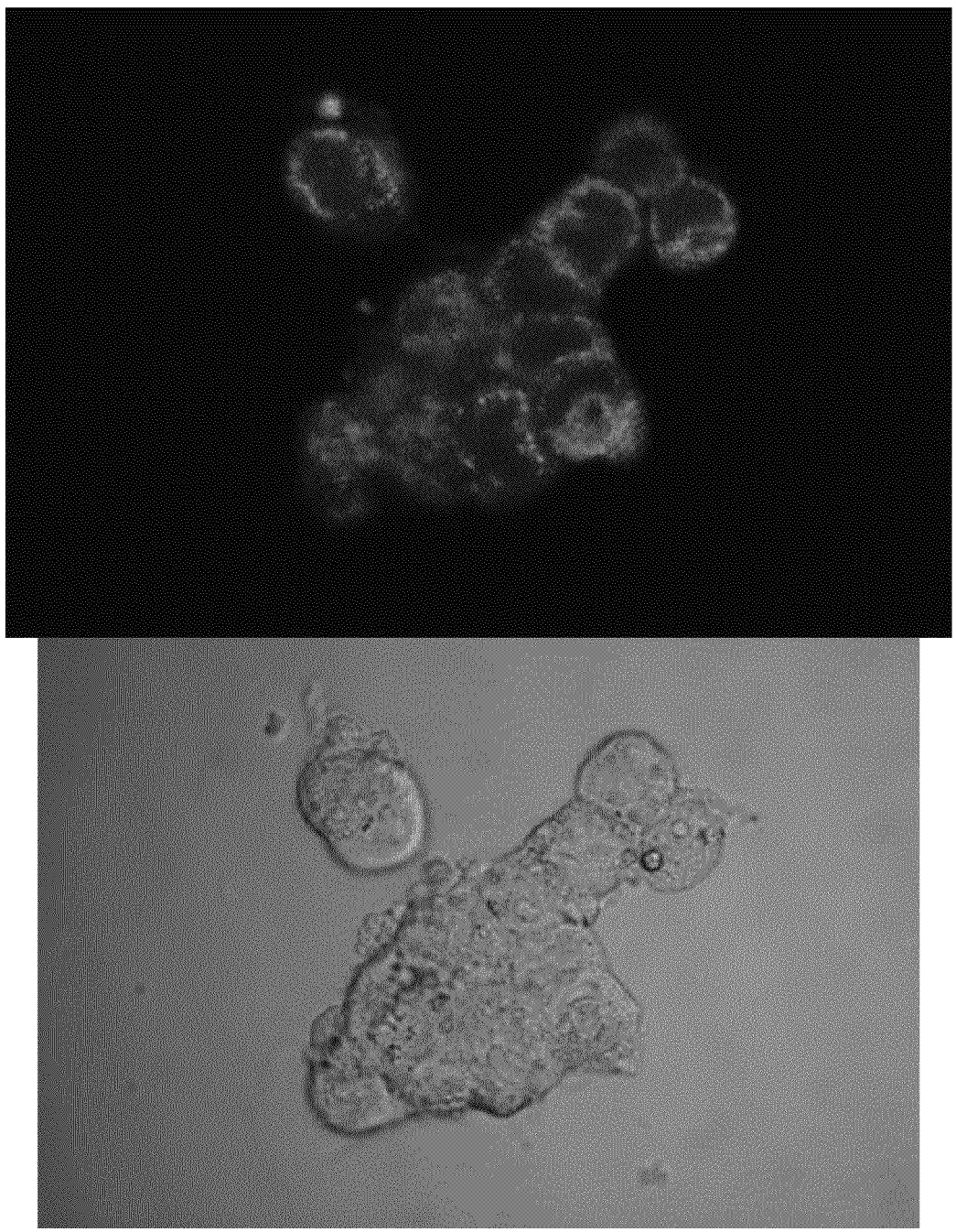
FIG. 12 is showing the fluorescence with the corresponding transmittance images of human liver cells (BNAL 2) incubated with p-phosphonated calyx[5]arene. Such fluorescence is much greater than the auto-fluorescence of such cell lines.

Phosphonated calix[5]arene was tested with flow cytometry at the following concentrations; 10-4M, 2.5×10-5M (1 in 4 dilution) and 3.13×10-6M (1 in 32 dilution). Lymphocyte and monocyte population characteristics are summarised in the graph in FIG. 9. Lymphocyte and monocyte population numbers are based on total population while apoptotic cells, dead cells, live cells etc are based on their respective populations. Lymphocytes normally make up 60% of total population. The proportion of dead lymphocytes seems to decline as the concentration increases. However, this is most likely due to total lysis of cells, which cannot be detected by dead cell marker. Monocytes normally make up 10-15% of total population. Culturing process seems to cause most monocytes to be apoptotic due to their fragile nature and this finding is in line with our literature review. There is a decline in monocyte numbers with increasing concentration of this calixarene. The live monocytes population numbers seems to increase with increasing concentration of calixarene.

It is to be understood that, although prior art use and publications may be referred to herein, such reference does not constitute an admission that any of these form a part of the common general knowledge in the art, in Australia or any other country.

For the purposes of this specification it will be clearly understood that the word "comprising" means "including but not limited to", and that the word "comprises" has a corresponding meaning.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

The invention claimed is:

1. A process for the preparation of phosphonated calix[n]arenes of formula (I):

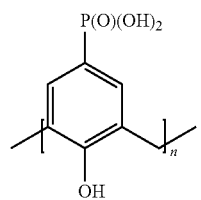

wherein n≧4, comprising the steps of:
a) reacting calix[n]arene with a source of leaving groups (Z) to produce compound (II),

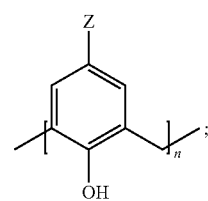

b) protecting p-hydroxyl groups of compound (II) to produce compound (III),

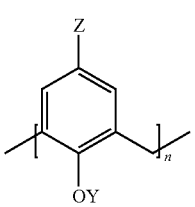

wherein Y is a protecting group;
c) reacting compound (III) with a phosphonating agent to produce compound (IV)

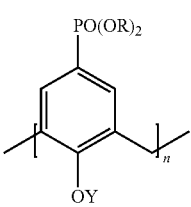

wherein R is an optionally substituted $C_1$-$C_8$ alkyl or an optionally substituted 5- or 6-membered aryl;

d) removing the protecting groups Y from compound (IV) to produce compound (V)

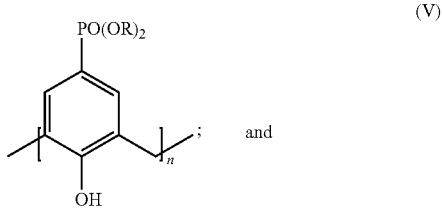

e) de-esterifying compound(V).

2. A process for the preparation of phosphonated calix[n]arenes of formula (I):

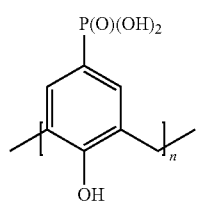

wherein n≧4 comprising the steps of:
a) protecting the hydroxyl group of a compound of formula (VI)

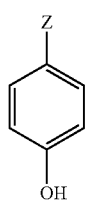

wherein Z is a leaving group to produce compound (VII),

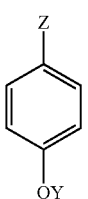

wherein Z is a leaving group and Y is a protecting group;
b) reacting a compound (VII) with a phosphonating agent to produce compound (VIII)

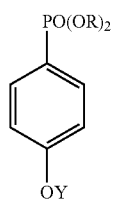

wherein Y is a protecting group and R is optionally substituted $C_1$-$C_8$ alkyl, or optionally substituted 5- or 6-membered aryl;

c) removing the protecting group Y from compound (VIII) to produce compound (IX)

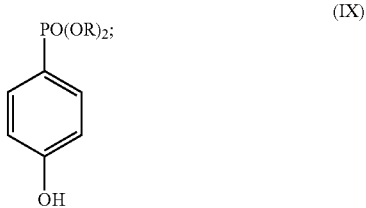

d) de-esterifying compound (IX) to produce compound (X)

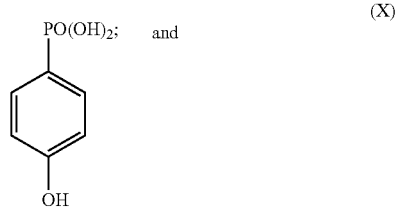

e) reacting compound (X) with formalin and cyclising 4 or more of these compounds.

3. A phosphonated calix[n]arene of formula (I):

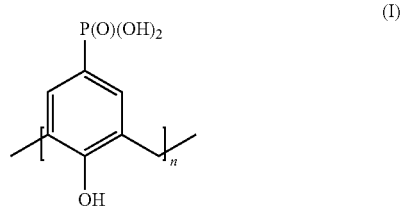

wherein n≧4, produced by the process method of claim 1.

4. A phosphonated calix[n]arene of formula (II):

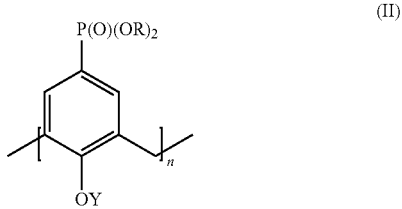

wherein n≧4, Y is a protecting group comprising —C—OR' wherein R' is an optionally substituted $C_1$-$C_8$ alkyl, and R is an optionally substituted $C_1$-$C_8$ alkyl, or an optionally substituted 5- or 6-membered aryl.

5. A bilayer of phosphonated calix[n]arenes with each layer comprising adjacent phosphonated calix[n]arenes of formula (I):

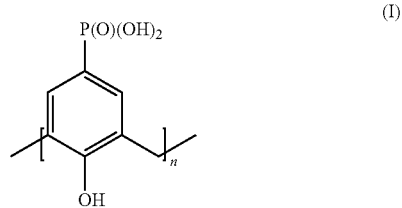

wherein n≧4,
with the two layers held together by a non-covalent bonding network.

6. A bilayer according to claim 5 wherein the non-covalent bonding network is directly between the phosphonate groups of the phosphonated calixarenes of each of the layers.

7. A bilayer according to claim 5 wherein the non-covalent bonding network is mediated by solvent molecules located between the bilayers.

8. An assembly comprising a plurality of the bilayers according to claim 5 wherein the plurality of bilayers are stacked together.

9. An assembly according to claim 8 which is a crystallographic assembly and the phosphonated calix[n]arene of formula (I) when n=4 has a crystallographically imposed symmetrical cone conformation and resides on a 4-fold symmetry axis with the tetragonal axis being located normal to the bilayers.

10. An assembly according to claim 8 which is a nanometer scale raft in which the plurality of bilayers are stacked together in the presence of a solvent which can be bound by the calix[n]arene of formula (I).

11. A process for the preparation of an assembly of stacked bilayers of phosphorated calix[n]arenes with each layer comprising adjacent phosphonated calix[n]arenes of formula (I):

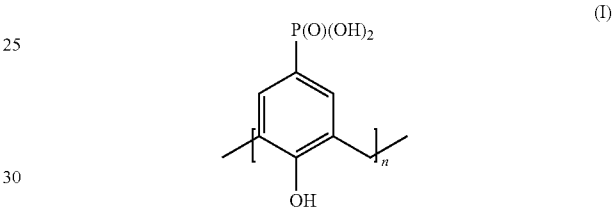

Wherein n ≧4, with the two layers held together by a non-covalent bonding network, said process comprising evaporating a solution of the calix[n]arene of formula (I), or subjecting a solution of the calix[n]arene of formula (I) to a region of high shear, or subjecting a precursor and/or reagents for the preparation of the calx[n]arine of formula (I) to a region of high shear.

12. A process for the preparation of the assembly according to claim 11, wherein the solution of calix[n]arine of formula (I) is subject to the region of high shear, and wherein the region of high shear is provided via a rotating surface reactor.

13. A process for preparation of the assembly according to claim 12 wherein the solution of the calix[n]arene of formula (I) is alkaline and is combined with an acid solution via the rotating surface reactor.

14. A process for preparation of the assembly according to claim 11, wherein the solution of calix[n]arene of formula (I) is subjected to the region of high shear, which takes place in the presence of a solvent which can bind in the cavity of the calixarene of formula (I).

15. The process according to claim 14, wherein the region of high shear is a rotating surface of a rotating surface reactor.

16. The process according to claim 11 wherein the precursor and/or reagents for the preparation of the calix[n]arene of formula (I) are subjected to the region of high shear, wherein the region of high shear is provided via a rotating surface reactor, and wherein the precursor and/or reagents are provided to the rotating surface reactor.

17. The process according to claim 11, wherein the solution of calix[n]arene of formula (I) is subjected to the region of high shear, which takes place in the presence of acetonitrile.

* * * * *